(12) United States Patent
Croce et al.

(10) Patent No.: US 6,924,414 B2
(45) Date of Patent: Aug. 2, 2005

(54) MUIR-TORRE-LIKE SYNDROME IN FHIT DEFICIENT MICE

(75) Inventors: Carlo M. Croce, Philadelphia, PA (US); Frances Kay Huebner, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/832,424

(22) Filed: Apr. 11, 2001

(65) Prior Publication Data

US 2002/0116726 A1 Aug. 22, 2002

Related U.S. Application Data

(60) Provisional application No. 60/196,534, filed on Apr. 11, 2000.

(51) Int. Cl.[7] .......................... C12N 15/00; A61K 67/00
(52) U.S. Cl. ................................ 800/18; 800/8; 800/3; 800/21
(58) Field of Search ........................... 800/18, 8, 3, 21, 800/9, 10, 13

(56) References Cited

U.S. PATENT DOCUMENTS

| | | | | |
|---|---|---|---|---|
| 5,087,571 A | | 2/1992 | Leder et al. | 435/240.2 |
| 5,698,766 A | * | 12/1997 | Julius et al. | 800/2 |
| 5,907,079 A | | 5/1999 | Mak et al. | 800/2 |
| 5,928,884 A | | 7/1999 | Croce et al. | 435/7.23 |
| 6,025,137 A | | 2/2000 | Shyjan | 435/6 |
| 6,242,212 B1 | | 6/2001 | Croce et al. | 435/69.1 |

OTHER PUBLICATIONS

Mullins, 1990, Nature, vol. 344, p. 541–544.*
Hammer, 1990, Cell, vol. 63,. p. 1099–1112.*
Mullins, 1989, EMBO Journal, vol. 8, p. 4065–4072.*
Taurog, 1988, J. Immunol., vol. 141, p. 4020–4023.*
Wall, 1996, Theriogenology, vol. 45, p. 57–68.*
Ebert, 1988, Mol. Endocrinology, vol. 2, p. 277–283.*
Overbeek, 1994, "Factors affecting transgenic animal production," Transgenic animal technology, pp. 96–98.*
Mullins, 1996, J. Clin. Invest., vol. 98, pp. S37–S40.*
Capecchi, 1994, Scientific American, vol. 270, p. 34–41.*
Pekarsky, 1998, Cancer Res., vol. 58, p. 3409–3414.*
Huebner et al. Annu. Rev. Genet. 1998. vol. 32, p. 7–31.*
Zanesi, PNAS, 2001, vol. 98, p. 10250–10255.*
Fong et al., "Induction of a Muir–Torre–like syndrome in Fhit deficient mice" (Abstract), *Proceedings of the American Association for Cancer Research Annual Meeting* (Mar. 2000) No. 41:68; 91st Annual Meeting of the American Association for Cancer Research, San Francisco, California USA (Apr. 1–5, 2000).
Fong and Magee, "Dietary zinc deficiency enhances esophageal cell proliferation and N–nitrosomethylbenzylamine (NMBA)–induced tumor incidence in C57BL/6 mouse", *Cancer Letters* 143:63–69 (1999).
Fong Louise Y Y et al., "Muir–Torre–like syndrome in Fhit–deficient mice", *Proceedings of the National Academy of Sciences of USA, National Academy of Science* (Apr. 25, 2000), pp. 4742–4747.
Dumon Kristoffel R et al., "FHIT gene therapy prevents tumor development in Fhit–deficient mice", *Proceedings of the National Academy of Sciences of USA, National Academy of Science* (Mar. 13, 2001), pp. 3346–3351.
Ji Lin et al., "Induction of apoptosis and inhibition of tumorigenicity and tumor growth by adenovirus vector–mediated fragile histidine triad (FHIT) gene overexpression", *Cancer Research, American Association for Cancer Research* (Jul. 15, 1999); vol. 59, No. 14, pp. 3333–3339.
Croce C M et al., "Role of Fhit in Human Cancer", *Journal of Clinical Oncology* (May 5, 1999); vol. 17, No. 5, pp. 1618–1624.

* cited by examiner

*Primary Examiner*—Michael C. Wilson
(74) *Attorney, Agent, or Firm*—Hamilton, Brook, Smith & Reynolds, P.C.

(57) ABSTRACT

The invention provides nonhuman transgenic animals with a disrupted FHIT gene. The invention further provides transgenic mice in which one or both Fhit alleles have been inactivated. Preferably, the Fhit-deficient mice develop multiple tumors of both visceral and sebaceous origin, similar to those of Muir-Torre familial cancer syndrome. The present invention further relates to the generation of these transgenic mice and their use as model systems to study the effects of carcinogenic agents in promoting clonal expansion of neoplastic cells in cancers, preferably gastrointestinal cancers of which Muir-Torre syndrome is a subset. The invention further relates to testing therapeutic agents for their efficacy in the prevention and treatment of cancer, preferably gastrointestinal cancer.

12 Claims, 7 Drawing Sheets

SEQUENCE LISTING

<160> NUMBER OF SEQ ID NOS: 11

<210> SEQ ID NO 1
<211> LENGTH: 27
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 1
cttgaatcta ggctgcattc tagcgag                                    27

<210> SEQ ID NO 2
<211> LENGTH: 27
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 2
gattccttgc ttaccttttg gggatgg                                    27

<210> SEQ ID NO 3
<211> LENGTH: 22
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 3
tgggctctat ggcttctgag gc                                         22

<210> SEQ ID NO 4
<211> LENGTH: 18

```
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 4
gtgttcttca cagttacg                                              18

<210> SEQ ID NO 5
<211> LENGTH: 20
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 5
caattctata cattctttgc                                            20

<210> SEQ ID NO 6
<211> LENGTH: 20
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 6
ggcctgctgg ataattcata                                            20

<210> SEQ ID NO 7
<211> LENGTH: 20
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 7
agataacata atgaaagagc                                            20

<210> SEQ ID NO 8
<211> LENGTH: 21
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 8
cactgtcaag tcaaaatata g                                          21

<210> SEQ ID NO 9
<211> LENGTH: 21
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 9
ggccttgtga ctaaataata a                                          21

<210> SEQ ID NO 10
<211> LENGTH: 19
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 10
```

```
-continued ctctctcctc caatgttat                                                    19

<210> SEQ ID NO 11
<211> LENGTH: 18
<212> TYPE: DNA
<213> ORGANISM: ARTIFICIAL SEQUENCE
<220> FEATURE:
<223> OTHER INFORMATION: DESCRIPTION OF ARTIFICIAL SEQUENCE: PRIMER

<400> SEQUENCE: 11
aaggttagca gaaagagg                                                     18
```

US 6,924,414 B2

MUIR-TORRE-LIKE SYNDROME IN FHIT DEFICIENT MICE

Figure 1:
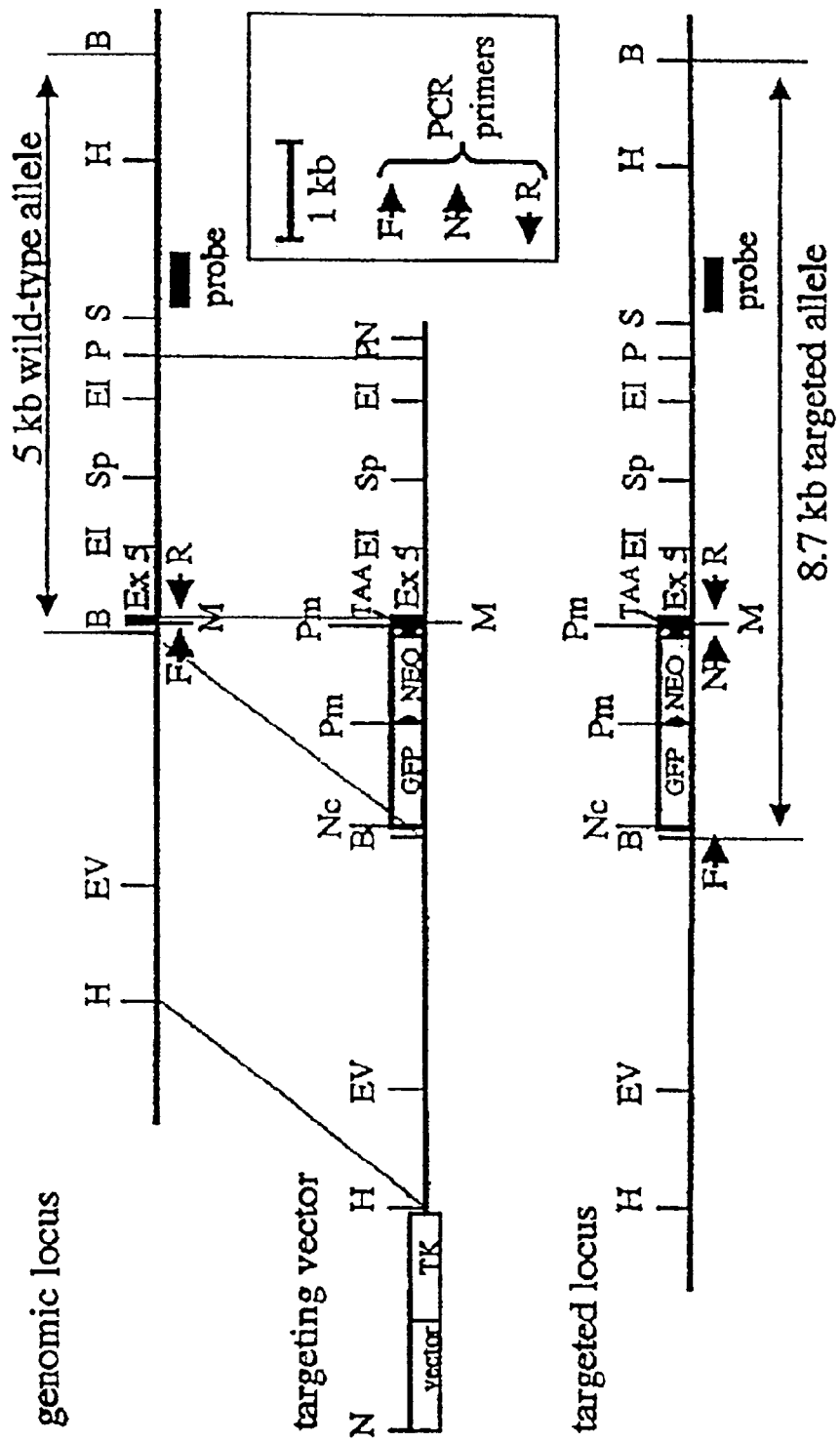

This application claims the benefit of U.S. Provisional Application No. 60/196,534 filed Apr. 11, 2000, which is incorporated by reference herein in its entirety.

This invention was made in part with government support under Grant numbers CA21124 and CA56336 awarded by the National Cancer Institute, USPHS; Grant number 97B115-REV from the American Institute for Cancer Research and Grant number ME99-105 from the Pennsylvania Department of Health. The Government has certain rights in the invention.

1. FIELD OF THE INVENTION

The present invention relates to the field of cancer biology, more particularly to transgenic animal that are predisposed to the development of multiple tumors and are useful as models for Muir-Torre familial cancer syndrome.

2. BACKGROUND OF THE INVENTION

Since it was first noted that human chromosomal fragile sites mapped to chromosome bands that were nonrandomly altered by translocations or deletions in neoplasias, it has been proposed that the recombinogenicity of fragile sites, possibly enhanced by environmental carcinogens, could lead to altered expression of oncogenes or tumor suppressor genes at fragile sites (Yunis and Soreng, 1984, Science 226:1199–1204). The corollary of the proposal is that alterations to expression of genes at fragile sites contribute to clonal expansion of the neoplastic cells. FHIT is thus far the only example of a gene at a constitutive fragile region and shows many hallmarks of a tumor suppressor gene (Ohta et al., 1996, Cell 84:587–597).

The FHIT gene is altered by deletion or translocation in a large fraction of many types of cancers, including lung, cervical, gastric and pancreatic (Ohta et al., 1996, Cell 84:587–597; Sozzi et al., 1996, Cell 85:17–26; Hendricks et al., 1997, Cancer Res. 57:2112–2115; Greenspan et al., 1997, Cancer Res. 57:4692–4698; Baffa et al., 1998, Cancer Res. 58:4708–4714; Simon et al., 1998 Cancer Res. 58:1538–1587; Sorio et al., 1999, Cancer Res. 59:1308–1314). FHIT protein is lost or reduced in the majority of these cancers, in a large fraction of other cancer types (Hadaczek et al., 1998, Cancer Res. 58:2946–295; Ingvarsson et al., 1999, Cancer Res. 59:2682–2689; van Heerden et al., 1999, J. Oral Path. Med. 28:433–437), and preneoplastic lesions in the lung (Sozzi et al., 1998, Cancer Res. 58:5032–5037). Nevertheless, acceptance of FHIT as a tumor suppressor has not been universal (Le Beau et al., 1998, Genes Chromosomes Cancer 21:281–289), with some reports suggesting that fragility of the locus alone could account for the occurrence of clonal or oligoclonal genetic alterations at FHIT in cancers. To define the role of FHIT protein in cancer development, a strain of Fhit-deficient mice was established. Surprisingly, these mice develop symptoms analogous to those seen in humans with Muir-Torre Syndrome (MTS), which is characterized by a predisposition for developing a combination of sebaceous and visceral tumors. The Fhit-deficient mice of the invention afford the opportunity for studying Muir-Torre Syndrome in a nonhuman animal.

Citation or discussion of a reference herein shall not be construed as an admission that such is prior art to the present invention.

3. SUMMARY OF THE INVENTION

The present invention provides an embryonic stem cell containing a disruption of the FHIT locus, wherein said disruption comprises a termination codon in an exon 5 coding region. The invention further provides a transgenic mammal comprising cells that contain a disruption of the FHIT locus, wherein said disruption comprises a termination codon in an exon 5 coding region. The FHIT disruption can be homozygous or heterozygous. In a preferred embodiment, the transgenic mammal is a mouse. In one embodiment, the mouse is chimeric for the disruption of the FHIT locus. In another embodiment, the germline and somatic cells of the mouse contain the disruption of the FHIT locus. Preferably, the mouse comprising the FHIT disruption is characterized by a predisposition to developing a spectrum of visceral and skin tumors, and/or by hypersensitivity to NMBA. In a specific embodiment, the mouse comprising the FHIT disruption further comprises a disruption in the MSH2 gene.

The present invention further provides cell culture prepared from cells of a transgenic mouse that is homozygous or heterozygous for the FHIT disruption The present invention yet further provides a method of testing carcinogenicity of a molecule, comprising administering said molecule to a Fhit-disrupted transgenic mouse and comparing the rate of tumor formation in said transgenic mouse with a control mouse of the same genotype to which the molecule is not administered, wherein an increased rate of tumor formation following administration of the molecule is indicative that the molecule is a carcinogen.

Alternatively, the invention provides a method of testing carcinogenicity of a molecule, comprising contacting the cell culture generated from a mouse homozygous or heterozygous for a Fhit disruption with said molecule and comparing the rate of proliferation of said cell culture with an untreated cell culture; wherein an increased rate of proliferation following exposure to the molecule is indicative that the molecule is a carcinogen.

The present invention further provides a method of testing the therapeutic efficacy of a molecule in treating or preventing cancer comprising administering said molecule to a Fhit-disrupted transgenic mouse and comparing the rate of tumor formation in said transgenic mouse with a control mouse of the same genotype to which the molecule is not administered, wherein a reduced rate of tumor formation following administration of the molecule is indicative that the molecule has therapeutic value for cancer.

Alternatively, the present invention provides a method of testing the therapeutic efficacy of a molecule in treating or preventing cancer comprising contacting the cell culture generated from a mouse homozygous or heterozygous for a Fhit disruption with said molecule and comparing the rate of proliferation of said cell culture with an untreated cell culture; wherein a reduced rate of cell proliferation following exposure to the molecule is indicative that the molecule has therapeutic value for cancer.

3.1 Abbreviations

NMBA: N, nitrosomethylbenzylamine
H & E: hematoxylin and eosin
MTS: Muir-Torre syndrome
MSI: Microsatellite instability

4. BRIEF DESCRIPTION OF THE DRAWINGS

FIG. 1: Murine FHIT genomic locus, targeting and screening strategy. The top line represents the FHIT genomic locus surrounding exon 5. The middle line depicts the targeting vector with a 6.6 kb HindIII (H)-Pst1 (P)

fragment with a termination codon introduced into exon 5. The targeted locus after homologous recombination is shown at the bottom with the probe used for Southern blot screening of ES colony and progeny DNA after BamHI (B) cleavage. Positions of the primers used for PCR-amplification of progeny DNA, to identify wild-type (F,R) and targeted (N,R) alleles, are shown. Restriction enzyme sites are shown for EcoRV (EV), EcoRI (E1), Sph1 (Sp), Sac1 (S), Not1 (N), Nco1 (Nc), Pme1 (Pm). The 5'®3' sequences of the three primers F, R and N are, respectively:

```
CTTGAATCTAGGCTGCATTCTAGCGAG      (SEQ. ID. NO.:1),
GATTCCTTGCTTACCTTTTGGGGATGG      (SEQ. ID. NO.:2),
and
TGGGCTCTATGGCTTCTGAGGC           (SEQ. ID. NO.:3),.
```

The first reaction product is a wild-type fragment of ~450 bp containing exon 5; the second product is a mutant fragment of ~280 bp spanning from the Neo selection gene to intron 5. PCR conditions were: denaturation 94° C., 30s; annealing 62° C., 30s; elongation 72° C., 30s; 35 cycles.

Figure 2:
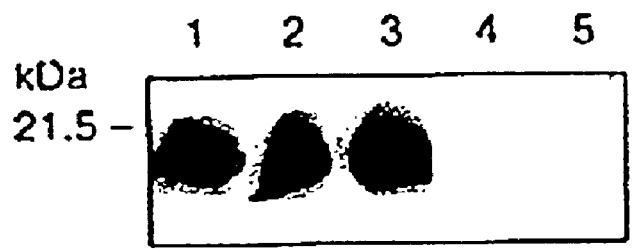

FIG. 2: Absence of FHIT protein in the Fhit –/– mice. Lysates from tissues of Fhit –/– mice were tested for expression of FHIT by immunoblot analysis of mouse tissue lysates: lane 1, FHIT +/+ lung; lane 2, +/+ liver; lane 3, +/+ kidney; lane 4, Fhit –/– liver; lane 5, –/– kidney.

Figure 3:
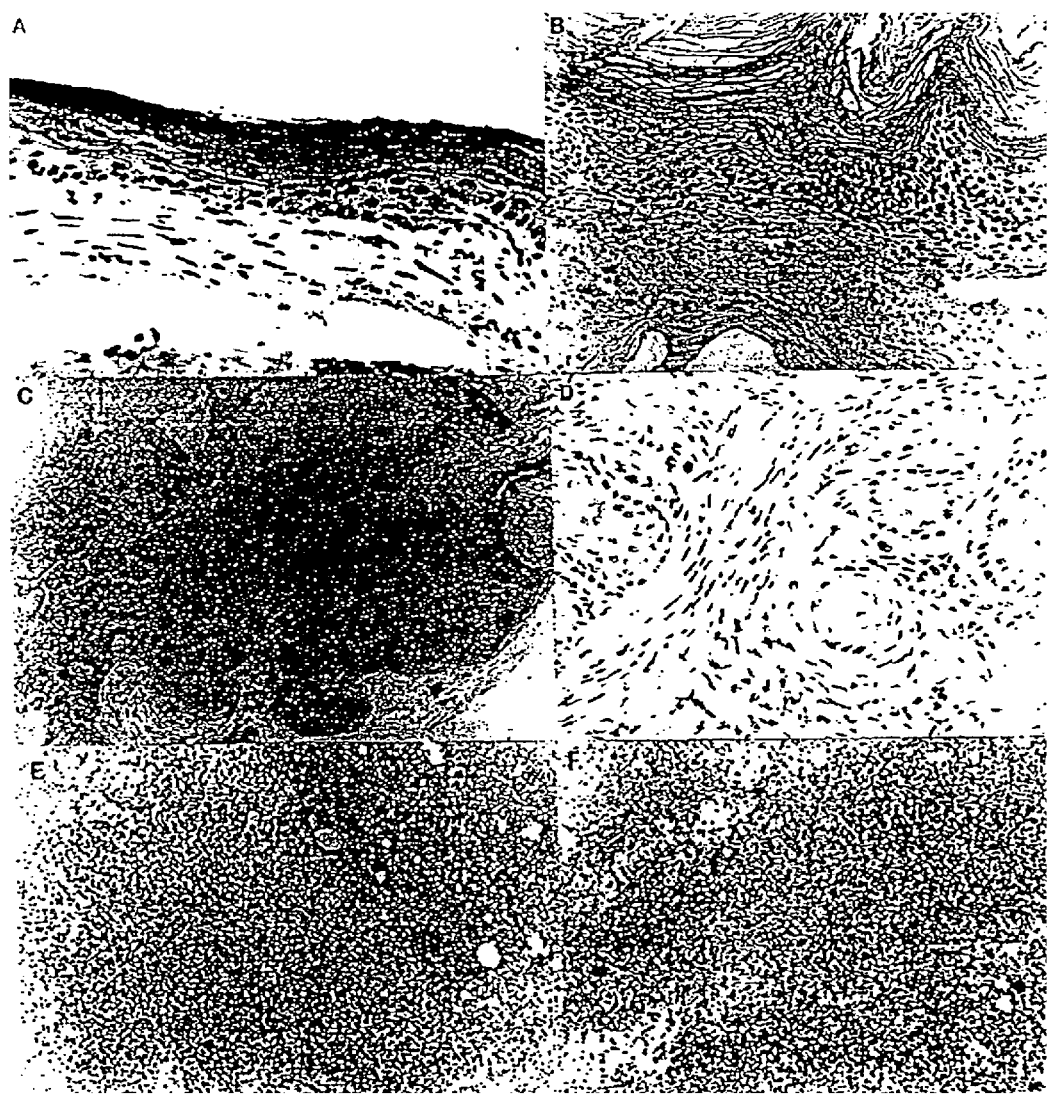

FIG. 3: Immunohistochemical detection of FHIT expression. A, FHIT expression in normal esophageal epithelium (200×) of FHIT +/+ mouse 23 at ten weeks post NMBA; the brown chromogen represents the FHIT protein. B, lack of FHIT expression in a squamous papilloma of the forestomach (200×) in Fhit +/– mouse 33 at ten weeks post NMBA; C, absence of FHIT expression in a squamous papilloma of the junction (200×) in FHIT +/+ mouse 25 at ten weeks post NMBA; D, lack of FHIT expression in an invasive squamous carcinoma of the forestomach (100×) in Fhit +/– mouse 31 at ten weeks post NMBA; E, lack of FHIT expression in a sebaceous tumor (100×) in Fhit +/– mouse 27 at ten weeks post NMBA; F, absence of FHIT protein in a sebaceous tumor (100×) in Fhit +/– mouse 21 at ten weeks post NMBA.

FIG. 4A-4D: Immunohistochemical detection of human FHIT in MTS tumors. A, FHIT expression in normal hair follicle (200×); note that dense keratin horn shows nonspecific staining; B, FHIT expression in normal sebaceous gland (200×); C, hematoxylin and eosin (H&E) staining of a Muir-Torre Syndrome case 1 sebaceous tumor; D, lack of FHIT expression in most cells of the case 1 sebaceous tumor.

Figure 5:
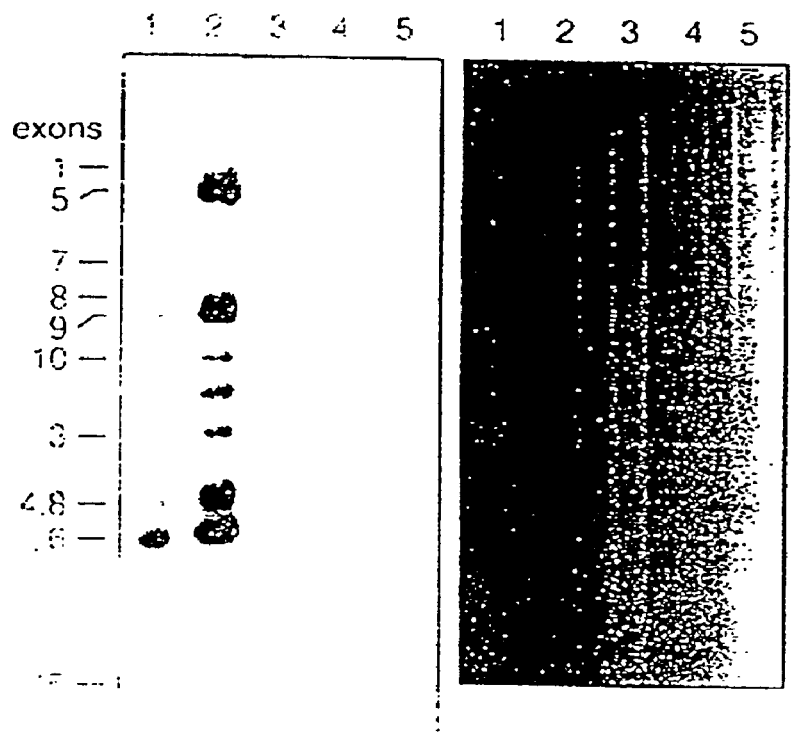

FIG. 5: Integrity of FHIT loci in murine tumors. DNA from tails and sebaceous tumors was cleaved with XbaI, electrophoresed, transferred to a membrane and hybridized to a $^{32}$P-labelled full length FHIT cDNA probe. FHIT exons are indicated on the left; the asterisk indicates the inactivated Fhit exon 5. Lanes 1, 3 and 4 contained DNAs from sebaceous tumors from Fhit +/– mice 21, 27 and 31; lane 2 contained DNA from the tail of FHIT +/+ mouse 25 and lane 5 contained DNA from a Swiss mouse 3T3 cell line, which exhibits a variant-sized exon 3 (obscured by another fragment) due to a polymorphism. The FHIT +/+ and +/– mice are B6129F1s which exhibit two different alleles of exon 8. The right panel shows the agarose gel prior to blotting of the digested DNAs to the membrane; this gel illustrates that amounts of DNA loaded in individual lanes varied from ~1 μg (lane 4) to ~10 μg (lane 2).

Figure 6:
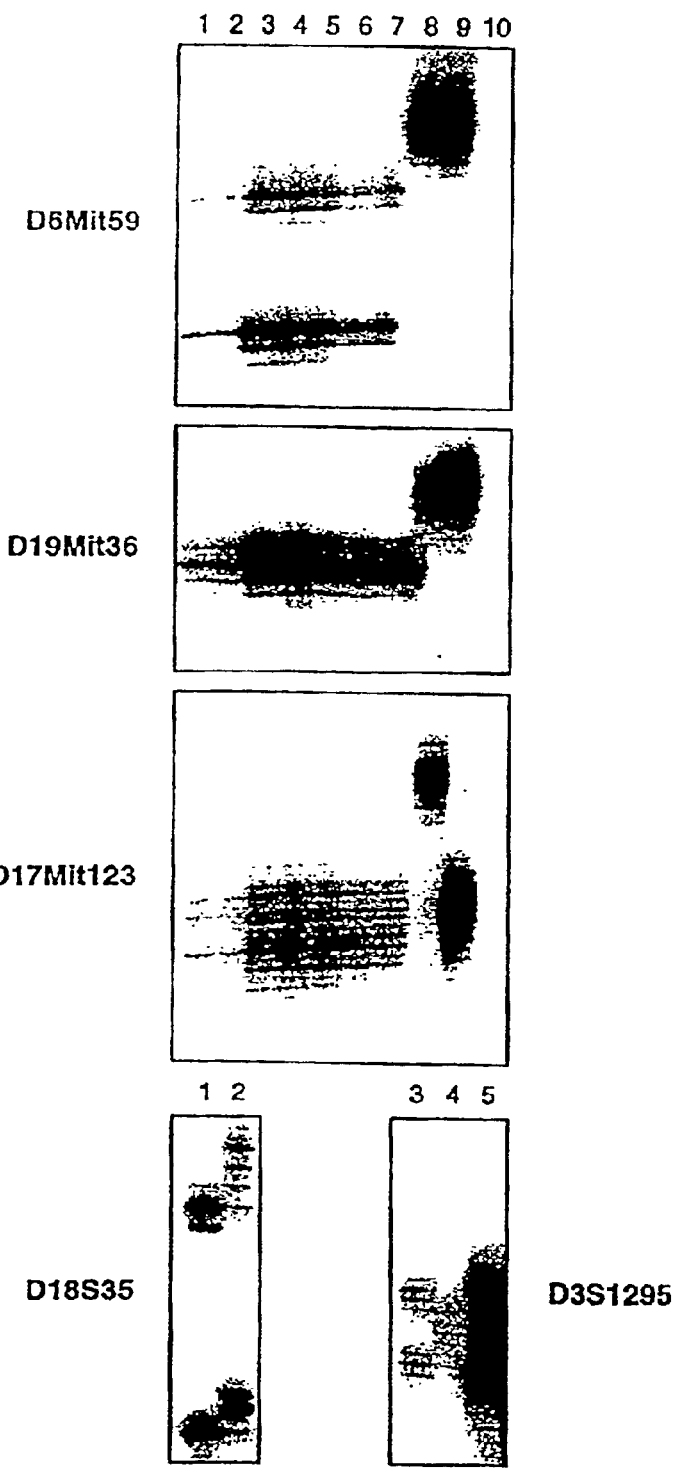

FIG. 6: Assessment of MSI in tumors. DNA templates from mouse and human tumors and controls were amplified using primers flanking microsatellite alleles. Labeled amplified products were run on PAGE gels, dried and exposed. The D6Mit59, D19Mit36 and D17Mit123 panels represent murine alleles amplified from Fhit +/– mouse 27 forestomach tumor (lane 1), FHIT +/+ mouse 25 forestomach tumor (lane 2), FHIT +/+ mouse 25 tail (lane 3), Fhit +/– mouse 21 sebaceous tumor (lane 4), Fhit +/– mouse 27 sebaceous tumor (lane 5), Fhit +/– mouse 27 second sebaceous tumor (lane 6), Fhit +/+ mouse 31 sebaceous tumor (lane 7), K1735 mouse melanoma cell line (lane 8), NP3 mouse cell line (lane 9), negative control (no DNA) (lane 10). No MSI was observed in the mouse tumors for the three markers shown. The D18535 and D3S1295 panels represent germline and tumor DNA from a human MTS case: DNA from peripheral blood lymphocytes (lane 1), DNA from sebaceous tumor 185 from the same individual (lane 2), lymphocyte DNA (lane 3) and DNA from sebaceous tumors 185 (lane 4) and 9029 (lane 5) from the same individual. These sebaceous tumors showed MSI at each allele successfully amplified.

Figure 7:
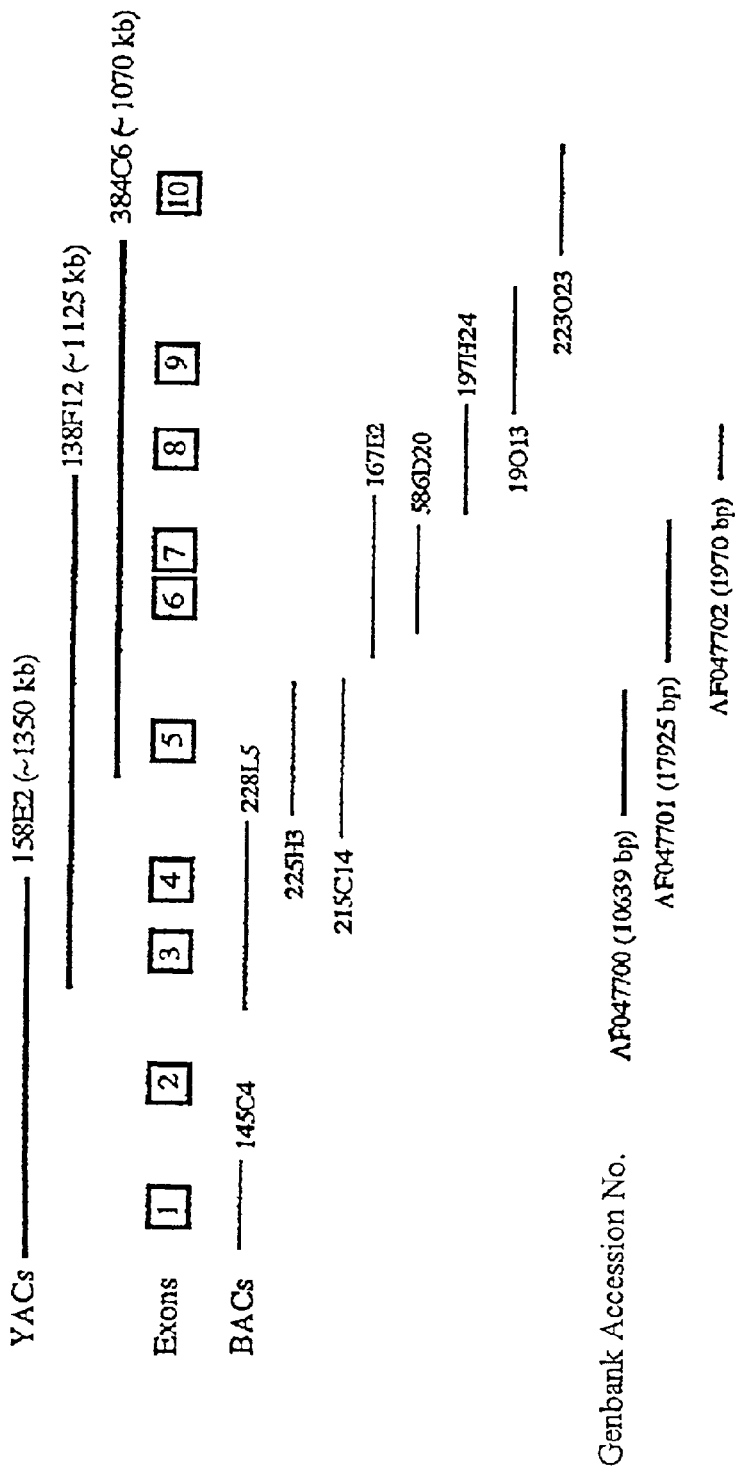

FIG. 7: A map of the murine genomic FHIT locus, indicating the relative positioning of exon sequences to yeast and bacterial artificial chromosomes (YACs and BACs, respectively). The regions of the mouse genomic FHIT locus whose sequences have been deposited in GenBank are indicated on the map by their GenBank accession numbers.

5. DETAILED DESCRIPTION OF THE INVENTION

The murine FHIT locus (FIG. 7; Pekarsky et al., 1998, Cancer Res. 58:3401–3408; Glover et al., 1998, Cancer Res. 58:3409–3414) is similar to its human homolog (U.S. Pat. No. 5,928,884), encompasses a common fragile site, and is altered in murine cancer cell lines. To define the role of FHIT protein in cancer development, a strain of Fhit +/– mice was established. The frequency of carcinogen-induced tumor formation in FHIT +/+ and +/– mice was compared using the established N-nitrosomethylbenzylamine (NMBA) esophageal/gastric cancer model (Fong and Magee, 1999, Cancer Letters 143:63–69).

Upon bioactivation, NMBA produces benzaldehyde and an electrophilic methylating agent (Labuc and Archer, 1982, Cancer Res. 42:3181–3186), which methylates DNA, resulting in the formation of the promutagenic, adduct 06-methylguanine (O6-meG) (Fong et al., 1979, Int. J. Cancer 23:679–682). NMBA was reported to induce both esophageal and forestomach tumors when administered by gavage or in the drinking water (Fong and Magee, 1999, Cancer Letters 143:63–69; Sander et al., 1973, 19:157–161). Fong and colleague have developed a model system that requires low doses of NMBA, based on their series of studies on esophageal tumor induction by NMBA in rats and mice (Fong and Magee, 1999, Cancer Letters 143:63–69; Fong et al., 1984, J. Natl. Cancer Inst. 72:419–425; Fong et al., 1997, Carcinogenesis 18:1477–1484). This model system was used to test the effects of NMBA administration on Fhit +/– mice. By ten weeks after NMBA exposure, all the Fhit +/– mice developed a spectrum of visceral and skin tumors similar to those observed in a human cancer syndrome, Muir-Torre Syndrome (MTS), a disease that is caused by deficiency in a mismatch repair gene.

Accordingly, the present is directed to the production of Fhit-deficient cells and Fhit-deficient nonhuman animals. The present invention is further directed to the use of the Fhit-deficient nonhuman animals as experimental models for the study of Muir-Torre Syndrome, and for testing potential carcinogenic and therapeutic agents.

The nonhuman transgenic animals contemplated by the present invention generally include any vertebrates, and preferably mammals, which encode a FHIT gene or homolog thereof. Such nonhuman transgenic animals may include, for example, transgenic pigs, transgenic rats, transgenic rabbits, transgenic cattle, transgenic goats, and other transgenic animal species, particularly mammalian species, known in the art. Additionally, other members of the rodent family, e.g. rat, and guinea pig, and nonhuman primates, such as chimpanzee, may be used to practice the present invention. Most preferred animals for the practice of the invention are mice.

With respect to a FHIT gene, the terms "functional disruption" or "functionally disrupted" as used herein mean that a FHIT locus comprises at least one mutation or structural alteration such that the functionally disrupted gene is substantially incapable of directing the efficient expression of functional gene product. By way of example but not limitation, an endogenous FHIT gene that has a stop codon introduced (optionally followed by a neo or other marker gene cassette) integrated into a coding exon (e.g., the fifth exon) that is not capable of encoding a functional FHIT protein, is therefore a functionally disrupted FHIT gene locus. Functional disruption can include the complete substitution of a FHIT gene by another gene, for example a reporter gene such as β-galactosidase, so that, for example, a targeting transgene that replaces the entire mouse FHIT open reading frame with a β-galactosidase open reading frame, is said to have functionally disrupted the endogenous murine β-galactosidase locus by displacing it. Deletion or interruption of essential transcriptional regulatory elements, polyadenylation signal(s), splicing site sequences will also yield a functionally disrupted gene. Functional disruption of an FHIT gene, may also be produced by other methods (e.g., antisense polynucleotide gene suppression). Also with respect to a FHIT gene, the term "structurally disrupted" refers to a targeted FHIT gene wherein at least one structural (i.e., exon) sequence has been altered by homologous gene targeting (e.g., by insertion, deletion, point mutation(s), and/or rearrangement). Typically, FHIT genes are functionally disrupted as a consequence of a disruption of the coding sequence; however FHIT genes may also be functionally disrupted without concomitantly being structurally disrupted, i.e., by targeted alteration of a non-coding sequence such as ablation of a promoter. An allele comprising a targeted alternation that interferes with the efficient expression of a functional geneproduct from the allele is referred to in the art as a "null allele".

With respect to a FHIT nucleic acid, the term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to", with respect to a FHIT gene, is used herein to mean that the complementary sequence is homologous to all or a portion of a reference FHIT polynucleotide sequence.

The terms "substantially corresponds to", "substantially homologous", or "substantial identity", when used in the context of a FHIT nucleic acid sequence, denotes a characteristic of the nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogenic DNA homology clamps, although it is recognized that the presence of various recombinases may reduce the degree of sequence identity required for efficient recombination.

The term "nonhomologous sequence", as used herein in reference to a FHIT nucleic acid, generally indicates that a sequence that is not substantially identical to a specified FHIT nucleic acid sequence.

"Specific hybridization" with reference to a FHIT nucleic acid sequence is defined herein as the formation of hybrids between a FHIT targeting transgene sequence (e.g., a FHIT polynucleotide which may include substitutions, deletion, and/or additions) and a specific target DNA sequence (e.g., a FHIT gene sequence). Specific hybridization can be tested with a labeled FHIT targeting transgene sequence to determine whether it preferentially hybridizes to the FHIT target such that, for example, a single band corresponding to a restriction fragment of a genomic FHIT gene can be identified on a Southern blot of DNA prepared from cells using said labeled targeting FHIT transgene sequence as a probe. It is evident that optimal hybridization conditions will vary depending upon the FHIT sequence composition and length (s) of the FHIT targeting transgene(s) and endogenous target(s), and the experimental method selected by the practitioner. Various guidelines may be used to select appropriate hybridization conditions (see, Maniatis et al., Molecular Cloning: A Laboratory Manual, 1989, 2nd Ed., Cold Spring Harbor, N.Y. and Berger and Kimmel, Methods in Enzymology, Volume 152. Guide to Molecular Cloning Techniques, 1987, Academic Press, Inc., San Diego, Calif.).

The term "naturally-occurring", in general and as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "targeting construct", when used herein in reference to a FHIT nucleic acid, generally refers to a polynucleotide which comprises: (1) at least one FHIT homology region having a sequence that is substantially identical to or substantially complementary to a sequence present in a host cell endogenous FHIT gene locus, and (2) a targeting region which becomes integrated into an host cell endogenous FHIT gene locus by homologous recombination between a targeting construct homology region and said endogenous FHIT gene locus sequence. If the targeting construct is a "hit-and-run" or "in-and-out" type construct (Valancius and Smithies, 1991, Mol. Cell. Biol. 11: 1402; Donehower et al., 1992, Nature 356: 215; Donehower, et al., 1991, J. NIH Res. 3: 59, the FHIT targeting region is only transiently incorporated into the endogenous FHIT gene locus and is eliminated from the host genome by selection. A FHIT targeting region may comprise a sequence that is substantially homologous to an endogenous FHIT gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein in reference to a FHIT nucleic acid, refer to a segment (i.e., a portion) of a FHIT targeting construct having a sequence that substantially corresponds to, or is substantially complementary to, a predetermined endogenous FHIT gene sequence, which can include sequences flanking said FHIT gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein. A homology clamp does not necessarily connote formation of a base-paired hybrid structure with an endogenous sequence. Endogenous FHIT gene sequences that substantially correspond to, or are substantially complementary to, a transgene homology region are referred to herein as "crossover target sequences" or "endogenous target sequences."

As used herein, the term "correctly targeted construct", when used in reference to a FHIT construct, refers to a portion of the targeting construct which is integrated within or adjacent to an endogenous crossover FHIT target sequence, such as a portion of an endogenous FHIT gene locus. By way of example but not limitation, a portion of a FHIT targeting transgene encoding neo and flanked by homology regions having substantial identity with endogenous FHIT gene sequences flanking the first exon, is correctly targeted when said transgene portion is integrated into a chromosomal location so as to replace, for example, the first exon of the endogenous FHIT gene. In contrast and also by way of example, if the targeting transgene or a portion thereof is integrated into a nonhomologous region and/or a region not within about 50 kb of a FHIT gene sequence, the resultant product is an incorrectly targeted FHIT transgene. It is possible to generate cells having both a correctly targeted FHIT transgene(s) and an incorrectly targeted FHIT transgene(s). Cells and animals having a correctly targeted FHIT transgene(s) and/or an incorrectly targeted FHIT transgene(s) may be identified and resolved by PCR and/or Southern blot analysis of genomic DNA.

As used herein, the term "targeting region", when used in reference to a FHIT targeting region, refers to a portion of a FHIT targeting construct that becomes integrated into an endogenous FHIT chromosomal location following homologous recombination between a homology clamp and an endogenous FHIT gene sequence. Typically, a FHIT targeting region is flanked on each side by a FHIT homology clamp, such that a double-crossover recombination between each of the homology clamps and their corresponding endogenous FHIT gene sequences results in replacement of the portion of the endogenous FHIT gene locus by the targeting region; in such double-crossover gene replacement targeting constructs the targeting region can be referred to as a "FHIT replacement region". However, some targeting constructs may employ only a single FHIT homology clamp (e.g., some "hit-and-run"-type vectors, see, Bradley et al., 1992, BioTechnology 10: 534).

As used herein, the term "replacement region", when used in the context of a FHIT transgene, refers to a portion of a FHIT targeting construct flanked by FHIT homology regions. Upon double-crossover homologous recombination between flanking homology regions and their corresponding endogenous FHIT gene crossover target sequences, the replacement region is integrated into the host cell chromosome between the endogenous crossover FHIT target sequences. Replacement regions can be homologous (e.g., have a sequence similar to the endogenous FHIT gene sequence but having a point mutation or missense mutation), nonhomologous (e.g., a neo gene expression cassette), or a combination of homologous and nonhomologous regions.

As used herein, the term "minigene", when used in reference to a FHIT minigene, refers to a heterologous gene construct wherein one or more nonessentiaL segments of a FHIT gene are deleted with respect to the naturally-occurring FHIT gene. Typically, deleted segments are intronic sequences of at least about 500 basepairs to several kilobases, and may span up to several tens of kilobases or more. Isolation and manipulation of large (i.e., greater than about 30–100 kilobases) targeting constructs is frequently difficult and may reduce the efficiency of transferring the targeting construct into a host cell. Thus, it is frequently desirable to reduce the size of a targeting construct by deleting one or more nonessential portions of a FHIT gene. Typically, intronic sequences that do not encompass essential regulatory elements may be deleted. For example, a FHIT minigene may comprise a deletion of an intronic segment between the fifth and sixth exons of the human FHIT gene. Frequently, if convenient restriction sites bound a nonessential intronic sequence of a cloned FHIT gene sequence, a deletion of the intronic sequence may be produced by: (1) digesting the cloned DNA with the appropriate restriction enzymes, (2) separating the restriction fragments (e.g., by electrophoresis), (3) isolating the restriction fragments encompassing the essential exons and regulatory elements, and (4) ligating the isolated restriction fragments to form a minigene wherein the exons are in the same linear order as is present in the germline copy of the naturally-occurring FHIT gene. Alternate methods for producing a minigene will be apparent to those of skill in the art (e.g., ligation of partial genomic clones which encompass essential exons but which lack portions of intronic sequence). Most typically, the gene segments comprising a minigene will be arranged in the same linear order as is present in the germline FHIT gene, however, this will not always be the case. Some desired regulatory elements (e.g., enhancers, silencers) may be relatively position-insensitive, so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some FHIT genes may have exons which are alternatively spliced at the RNA level, and thus a minigene may have fewer exons and/or exons in a different linear order than the corresponding germline FHIT gene and still encode a functional gene product. A cDNA encoding a FHIT gene product may also be used to construct a minigene.

As used herein, Fhit-deficient means that at least one of the two wild-type FHIT chromosomal alleles has been mutated such that less than wild-type levels of FHIT activity are produced. The term "Fhit deficient" includes both homozygous FHIT mutant cells and animals, as well as cells that are heterozygous for the FHIT mutant genotype.

Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document.

Preferred embodiments of the present invention include diploid mouse cells, mouse embryos, and mice that contain two chromosomal alleles of the FHIT gene, wherein at least one of the FHIT alleles contains a mutation such said cell produces less than wild-type levels of FHIT activity. Such FHIT deficient animals and cells are deemed to be useful as, inter alia, disease models for the analysis and testing of therapeutic agents, and the effects of mutagenic stimuli such as radiation and chemical mutagens. In a preferred embodiment, the FHIT mutation is a substitution mutation that results in a stop codon in the open reading frame of exon 5.

Mismatch repair is a process common to cells that probably functions as a control against tumor formation. Given that FHIT deficient animals are predisposed to the development of multiple tumors similar to those seen in Muir-Torre Syndrome, the presently described cells and animals are also deemed to be useful for the study of Muir-Torre Syndrome, and agents for treating the same.

In particular, methods are contemplated for screening for conditions that rescue the proliferation abnormalities of FHIT deficient cells or organisms. Examples of such conditions include, but are not limited to, the presence of exogenously added protein or chemical factors, the over expression of transfected genes or endogenous genes, or the ectopic expression of transfected genes or endogenous genes, or the mutagenesis of genes and the like.

The mutation, or targeted disruption, in the FHIT gene may be engineered using any of a number of well established mutations that are well known in the art. Preferably, the mutation shall be a substitution mutation, most preferably a substitution mutation that results in a termination codon of the FHIT open reading frame, although deletion mutations and/or insertion mutations are included within the scope of the present invention. Substitution mutations can be prepared by site directed mutagenesis, as described by (Hasty et al., 1991, Nature 350:243–246), that introduces a stop codon or other mutation near the 5' end of the FHIT gene such that abortive production of FHIT protein results, or the production of a mutant protein which lacks FHIT activity.

Similarly, insertion mutations can be introduced within the FHIT gene by taking advantage of the convenient restriction sites therein, such as any of the exonic restrictions sites or other sites which are easily identified by exonic sequencing of the FHIT gene and restriction mapping, and the techniques described by (Hasty et al., 1991, Molecular and Cellular Biology 11:4509–4517; Joyner et al., 1989, Nature 338:153–156). Another method of introducing an insertion or other mutation consists of infecting with a retrovirus which integrates in the FHIT locus, thereby creating a mutated Fhit allele as described by von Melchner et al., Genes and Development 6:919–927. In other embodiments, the mutants of the present invention preferably lack part of the DNA sequence coding for the FHIT protein (i.e., deletion mutants) so that a defective FHIT allele is more likely made. An additional feature of deletion mutants are that, relative to the insertion mutants taught by von Melchner, there is a drastically reduced possibility of reversion to the non-mutant allele. Deletion mutants can be produced by eliminating a DNA fragment from a coding region of the FHIT gene so that proper folding or substrate binding of the FHIT protein is prevented. The size of the deletion may vary, but in general a larger deletion is preferable to a smaller deletion since the larger deletions are more likely to result in a deficiency in FHIT activity. Typically, deletion mutations shall involve the excision of 1 base or up to essentially all of the bases of a given gene (including non-coding flanking regions). Alternatively, deleting a single base pair or two base pairs or any number of base pairs not divisible by 3 from the coding region would result in a frameshift mutation which would most likely be deleterious to making a functional FHIT protein. In the latter instance, a truncated polypeptide may be produced because polypeptide synthesis is aborted due to a frame shift-induced stop codon. For a general review of mutagenesis and mutation see "An Introduction to Genetic Analysis", 4th edition, 1989 (D. Suzuki, A. Griffiths, J. Miller, and R. Lewontin, eds.), W. H. Freeman & Co., N.Y., N.Y.

Changing a single base pair (or multiple base pairs) in the coding region of the FHIT gene may also cause a mutation which, if resulting in an amino acid change, may alter the proper folding of the FHIT protein and thereby create a Fhit deficiency. A single amino acid change so generated could also alter the activity of a FHIT protein. Another alternative would be to generate a deletion or other mutation in the non-coding region of the FHIT gene which affected the proper splicing of the FHIT messenger RNA. Such a mutation could effectively create a mutant FHIT transcript which was missing an entire exon or several exons as compared to the wild type FHIT message. Another alternative is to delete a non-coding regulatory region to decrease expression of the FHIT gene. The preferred size of the deletion is about several hundred nucleotides near the 5' end of the gene. Preferably, such a deletion would eliminate a number of nucleotides from the coding region not evenly divisible by 3, thereby creating a frameshift mutation as well. Alternatively, promoter sequences could be deleted or altered that would diminish transcription of the FHIT gene.

It is also possible to alter the expression of a given gene by altering the codon usage in the gene. Alterations of this sort preserve the amino acid sequence of the product while increasing or decreasing the levels of expression.

Antisense transgenes comprising antisense polynucleotides may also be employed to partially or totally knock-out expression of specific genes (Helene and Toulme, 1990, Biochimica Bioshys. Acta 1049:99; Pepin et al., 1991, Nature 355:725; Stout and Caskey, 1990, Somat. Cell Mol.

"Antisense polynucleotides" are polynucleotides that: (1) are complementary to all or part of a reference target sequence, such as the sequence of the FHIT gene, and specifically hybridize to a complementary target sequence, such as a chromosomal gene locus mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include antisense RNA which can hybridize specifically to individual mRNA species and hinder or prevent transcription and/or RNA processing of the mRNA species and/or translation of the encoded polypeptide (Ching et al., 1989, Proc. Natl. Acad. Sci. USA 86:10006–10010; Broder et al., Ann. Int. Med. 113:604–618; Loreau et al., 1990, FEBS Letters 274:53–56; Holcenberg et al., WO91/11535; WO91/09865; WO91/04753; WO90/13641; and EP 386563). An antisense sequence is a polynucleotide sequence of at least about 15 contiguous nucleotides in length, typically at least 20 to 30 nucleotides in length, and preferably more than about 30 nucleotides in length that is substantially complementary to a target gene sequence, or sequences, in a cell. In some embodiments, antisense sequences may have substitutions, additions, or deletions as compared to the complementary target sequence but as long as specific hybridization is retained, the polynucleotide will generally function as an antisense inhibitor of gene expression.

For the purposes of the present invention, the antisense sequence is complementary to an endogenous FHIT target gene sequence. In some cases, sense sequences corresponding to the FHIT target region sequence may function to suppress expression, particularly by interfering with transcription. Alternatively, an antisense polynucleotide will generally suppress FHIT expression at a post transcriptional level.

Given that antisense polynucleotides inhibit the production of the polypeptide(s) in cells, they may further alter a nonhuman transgenic animal's capacity to produce FHIT protein.

Antisense polynucleotides may be produced from a heterologous expression cassette inserted into transgenic pluripotent embryonic stem cells which may subsequently be used to generate the presently described Fhit-deficient animals.

5.1 FHIT Gene Sequences

The invention encompasses methods to produce nonhuman animals (e.g., non-primate mammals) that have at least one FHIT locus inactivated by gene targeting with a homologous recombination targeting construct. Any FHIT gene can be functionally disrupted according to the methods of the invention, provided that polynucleotide sequences that can be used as homology clamps in a targeting construct can be obtained (e.g., from GenBank database, in literature publications, or by routine cloning and sequencing, etc.). Typically, a FHIT gene sequence is used as a basis for producing PCR primers that flank a region that will be used as a homology clamp in a targeting construct. The PCR primers are then used to amplify, by high fidelity PCR amplification (Mattila et al., 1991, Nucleic Acids Res. 19: 4967; Eckert and Kunkel, 1991, PCR Methods and Applications 1: 17; U.S. Pat. No. 4,683,202, a genomic sequence from a genomic clone library or from a preparation of genomic DNA, preferably from the strain of nonhuman animal that is to be targeted with the targeting construct. The amplified DNA is then used as a homology clamp and/or targeting region. Thus, homology clamps for targeting essentially any FHIT gene may be readily produced on the basis of nucleotide sequence information available in the art and/or by routine cloning. General principles regarding the construction of targeting constructs and selection methods are reviewed in Bradley et al., 1992, BioTechnology 10: 534.

5.2 Fhit Mutations for Targeting Construct

Targeting constructs can be transferred into pluripotent stem cells, such as murine embryonal stem cells, wherein the targeting constructs homologously recombine with a portion of an endogenous FHIT gene locus and create mutation(s) (i.e., insertions, deletions, rearrangements, sequence replacements, and/or point mutations) which prevent the functional expression of the endogenous FHIT gene. A preferred method of the invention is to delete, by targeted homologous recombination, essential structural elements of an endogenous FHIT gene. For example, a targeting construct can homologously recombine with an endogenous FHIT gene and delete a portion spanning substantially all of one or more of the exons to create an exon-depleted allele, typically by inserting a replacement region lacking the corresponding exon(s). Transgenic animals homozygous for the exon-depleted allele (e.g., by breeding of heterozygotes to each other) are essentially incapable of expressing a functional endogenous FHIT molecule. Similarly, homologous gene targeting can be used, if desired, to functionally disrupt a FHIT gene by deleting only a portion of an exon of an endogenous FHIT gene. Targeting constructs can also be used to delete essential regulatory elements of a FHIT gene, such as promoters, enhancers, splice sites, polyadenylation sites, and other regulatory sequences, including sequences that occur up stream or downstream of the FHIT structural gene but which participate in FHIT gene expression. Deletion of regulatory elements is typically accomplished by inserting, by homologous double-crossover recombination, a replacement region lacking the corresponding regulatory element(s).

An alternative preferred method of the invention is to interrupt essential structural and/or regulatory elements of an endogenous FHIT gene by targeted insertion of a polynucleotide sequence, and thereby functionally disrupt the endogenous FHIT gene. For example, a targeting construct can homologously recombine with an endogenous FHIT gene and insert a nonhomologous sequence, such as a neo expression cassette, into a structural element (e.g., an exon) and/or regulatory element (e.g., enhancer, promoter, splice site, polyadenylation site) to yield a targeted FHIT allele having an insertional interruption. The inserted sequence can range in size from about 1 nucleotide (e.g., to produce a frameshift in an exon sequence) to several kilobases or more, as limited by efficiency of homologous gene targeting with targeting constructs having a long nonhomologous replacement region.

Targeting constructs of the invention can also be employed to replace a portion of an endogenous FHIT gene with an exogenous sequence (i.e., a portion of a targeting transgene); for example, the fifth exon of a FHIT gene may be replaced with a substantially identical portion that contains a nonsense or missense mutation.

Inactivation of a FHIT locus is achieved by targeted disruption of the gene by homologous recombination in mouse embryonic stem cells. For inactivation, any targeting construct that produces a genetic alteration in the target FHIT gene locus resulting in the prevention of effective expression of a functional gene product of that locus may be employed. If only regulatory elements are targeted, some low-level expression of the targeted gene may occur (i.e., the targeted allele is "leaky"), however the level of expression may be sufficiently low that the leaky targeted allele is functionally disrupted.

5.3 Gene Targeting

Gene targeting, which is a method of using homologous recombination to modify a mammalian genome, can be used to introduce changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert additional sequences, such as a positive selection marker, into coding elements of the target gene, thereby functionally disrupting it. Targeting constructs usually are insertion-type ("knock in") or replacement-type constructs ("knock out"; Hasty et al., 1991, Mol. Cell. Biol. 11: 4509).

The Fhit-deficient animals and cells of the present invention can be prepared by any of several techniques that are well established in the art including but not limited to those cited above. For example, techniques similar to those taught in U.S. Pat. No. 5,464,764 to Capecchi may be used. In general, Fhit defective cells may be engineered using the following steps:

(1) Constructing a targeting vector comprising a cloning vector and a DNA fragment containing at least one positively selectable marker gene (positive selection marker), flanked by two regions of the animal's FHIT gene or genomic locus which are in the same 5' to 3' orientation to one another (referred to as the regions of homology);

(2) Included in the targeting vector is a negatively selectable marker gene (negative selection marker) adjacent to one of the regions of homology. This negatively selectable marker may increase the likelihood of recovering the desired homologous recombination event (deleting a portion of the FHIT gene) but it is not required;

(3) Transfecting FHIT +/+ animal cells with the targeting vector of step (2);

(4) Selecting the transfected cells from step 3 for the marker(s) on the vector; and (5) Screening for Fhit-deficient animal cells from those cells in step (4) which are found to contain or express said positive selection marker(s), and not express said negative selection marker(s).

5.4 Targeting Constructs

The precise FHIT gene or gene locus sequences which must be present in the targeting vector of step (1) will depend on the sequences chosen for the modification of the FHIT locus, and (2) the restriction nucleases to be employed in the engineering of the mutant.

The specific regions of homology required in step (1) depend on the specifics of the deletion in the targeting vector. In general, the homology regions used in the targeting vector will preferably comprise at least about 100 bp, more preferably at least about 250 to 500 bp, more preferably at least 1000 bp, and most preferably at least about 1.5 kb or greater to insure a high degree of targeting efficiency.

Wherein the Fhit mutation created is a deletion mutation, the size of the deletion may also vary and depends on the regions of homology used in the targeting vector. Since non-contiguous regions of homology are used in the deletion targeting vector, that region in the wild-type allele which is located between the regions of homology constitutes the region to be deleted after homologous recombination with the targeting vector. Generally, it is preferable to delete at least a portion of an exon of the FHIT gene, or an entire exon, which results in a correspondingly mutated FHIT messenger RNA.

The particular positive and negative selection markers employed in the present invention are not critical to the practice of the invention. The positive selectable marker are located between the regions of homology and the negative marker, if one is used, are outside the regions of homology. The regions of homology are generally present in the vector in the same 5' to 3' orientation relative to one another. Conversely, the relative orientations of the positive and negative selectable markers are not critical. While it is not necessary to include a negative selectable marker, the presence of a negative marker may improve selection for targeted clones.

Preferably, the positive selectable marker is expressed in the cells that are targeted for gene modification. Positive and/or negative selection markers are deemed to be functional in the transfected cells if the DNA sequences encoding the selectable markers are capable of conferring either a positive or negative phenotypic selection characteristic to cells expressing the sequences. In general, the marker will be operably linked to a regulatory sequence that mediates the expression of the marker. A nucleic acid marker is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous.

Additionally, the means by which the positive selectable marker gene is made functional is not critical to the present invention. Positive selection is accomplished by exposing the cells to an appropriate agent which kills or otherwise selects against cells that do not contain or express an integrated positive selection marker. The positive selectable marker gene may have a promoter driving its expression or it may be driven by the juxtaposition of transcriptional elements at the target locus with the positive selectable marker. The latter gene organization requires that the transcriptional elements are active in the transfected cells.

In addition to a positive selection marker, the mutation engineered into the targeting vector may contain DNA sequence, e.g., an oligonucleotide linker, between the regions of FHIT gene homology in place of the deleted FHIT DNA. The oligonucleotide linker is generally about 8–10 nucleotides in length, but can be longer, e.g. about 50 nucleotides, or shorter, e.g. 4, 5 or 7 nucleotides. The preferred length of the oligonucleotide linker is about 20 to 40 nucleotides in length. The DNA sequence of the oligonucleotide linker is not critical.

The method of inserting the oligonucleotide between the regions of homology in the targeting vector DNA will depend upon the type of oligonucleotide linker used. Palindromic double stranded linkers containing one or more restriction nuclease sites in the oligonucleotide sequence (New England Biolabs) may be inserted by well known procedures (Maniatis et al., 1982, *Molecular Cloning*, Cold Spring Harbor Laboratory, Cold Spring Harbor Press, N.Y.)

Oligonucleotide linkers may also be inserted into deletions in plasmid DNA by tailing ends with complementary homopolymers using terminal transferase (Maniatis et al., supra), or a single stranded oligonucleotide linker may be inserted into a deletion in a plasmid by bridging, through annealing of an oligonucleotide containing ends complementary, to a cleaved plasmid's 3'-recessed and 3'-protruding cohesive ends, followed by filling-in the gap complementary to the oligonucleotide sequence with DNA polymerase (Klenow fragment). After subsequent ligation with T4 DNA ligase, closed circular DNA molecules can be regenerated.

Alternatively, site-directed mutagenesis may be used to simultaneously construct a specific deletion and insert a linker sequence by using a single stranded oligonucleotide to "loop-out" the desired region of the target gene (Krogstad and Champoux, 1990, J. Virol. 64(6):2796–2801.

If the targeting vector is designed such that the deleted region interrupts an exon, by the judicious choice of oligonucleotide linker length and sequence, frame shift mutations and/or stop codons may be produced in the FHIT gene in addition to the deletion within the FHIT gene.

The mutation engineered in the targeting vector may contain DNA sequences between the regions of FHIT gene homology in addition to the positive selection marker, for example, splice acceptor sequences. Such sequences have been shown to result in aberrant, and hence nonfunctional, mRNAs.

The DNA sequences used in the regions of homology are generally derived from FHIT gene sequence, sequences that flank the FHIT gene locus, or a combination thereof. Where an Fhit-deficient mouse is desired, the strain of mouse from which the FHIT DNA is derived is not critical, but preferably the gene is from the same as the strain of mouse as the cells targeted for gene transfer. Using DNA (in the regions of homology) that is isogenic to the target cells will generally enhance the efficiency of gene targeting. The regions of homology may be derived from genomic libraries of mouse DNA which may be cloned into a variety of cloning vectors such as lambda phage vectors, cosmid vectors, plasmid vectors, p1 phage vectors, yeast artificial chromosome vectors, and the like. Regions of homology to be incorporated into the targeting vector may also be derived from genomic DNA using polymerase chain reaction (PCR). Regions of homology so derived could be subcloned directly into the targeting vector. Alternatively, the regions of homology may be derived from an appropriate cDNA library.

5.4.1 Targeting Vectors

Any of a wide variety of cloning vectors may be used to construct the FHIT-targeting vectors of the present invention. Examples of such cloning vectors include, but are not limited to, pBR322 and pBR322-based vectors (Sekiguchi, 1983, Gene 21:267), pMB9, pBR325, pKH47 (Bethesda Research Laboratories), pBR328, pHC79, phage Charon 28 (Bethesda Research Laboratories, Boehringer Mannhein Biochemicals), pKB11, pKSV-10 (P-L Biochemicals), and oligonucleotide (dg)-tailed pBR322 (Bethesda Research Laboratories), pBluescript or similar plasmids (Stratagene), pK19 or related plasmids (New England Biolabs), the pUC series of plasmids (New England Biolabs), the pGEM series of plasmids (Promega), and the like.

As discussed above, the targeting vector will generally comprise two regions of FHIT homology separated by a positive selectable marker, and, optionally, a flanking negative selectable marker that is not critical as long as the cloning vector contains a gene expressing a selectable trait, e.g. drug resistance. The targeting vector may also be cloned into other cloning vectors such as such as lambda phage vectors, cosmid vectors, plasmid vectors, p1 phage vectors, yeast artificial chromosome vectors, and the like.

Another option is to prepare the components of the targeting vector synthetically by PCR and simply ligating each component such that the positive selectable marker is placed between the regions of homology, and the homology regions are place in the proper orientation relative to one another.

Any of a variety of restriction nucleases may be employed to produce fragments containing a FHIT gene. Thus, a FHIT gene restriction map provides guidance as to which of a wide variety of cloning vectors may be used to conveniently practice the present invention. In fact, many combinations of restriction endonucleases could be used to generate an FHIT targeting vector to mutate the FHIT gene. For example, a suitable restriction site in the murine FHIT gene is BamH1.

The specific host employed for growing the targeting vectors of the present invention is not critical, but the host will preferable have a functional hsd modification system. Examples of such hosts include *E. coli* K12 RR1 (Bolivar et al., 1977, Gene 2:95); *E. coli* K12 HB101 (ATCC No. 33694); *E. coli* MM21 (ATCC No. 336780); and *E. coli* DH1 (ATCC No. 33849). The preferred host in the present invention is *E. coli* strain DH5α (Life Technologies). Similarly, alternative vector/cloning systems could be employed such as targeting vectors which grow in *E. coli* or *Saccharomyces cerevisiae*, or both, or plasmid vectors which grow in *B. subtilus* (Ure et al., 1983, Methods in Enzymology, "Recombinant DNA", vol. 101, Part C, Academic Press, N.Y.).

5.5 Inducible and Tissue- and Developmental Stage-Specific Targeting of FHIT

In certain embodiments of the present invention, the Fhit-deficiency in FHIT transgenic animals is limited to specific developmental stages or to specific tissues. In another embodiment, Fhit-deficiency in FHIT transgenic animals or cells derived from FHIT transgenic animals is inducible.

Wherein the Fhit-deficiency is desired to be temporally or developmentally regulated, the Cre-Lox system may be employed. The Cre-Lox system may be used to activate or inactivate the FHIT gene at a specific developmental stage or in a particular tissue. Generally, methods utilizing Cre-Lox technology are carried out as described by Torres and Kuhn, 1997, "Laboratory Protocols for Conditional Gene Targeting", Oxford University Press. Methodology similar to that described for the Cre-Lox system can be employed utilizing the FLP-FRT system For inactivation of FHIT gene expression at a specific stage in development or a particular tissue, the FHIT coding region is replaced by a cassette comprising the coding region flanked by LoxP cites according to the methods described herein. The LoxP sites are targets for the Cre recombinase. The resulting transgenic animal is crossed to another transgenic animal in which the Cre recombinase is expressed under the control of a spatially and/or temporally regulated promoter. When Cre expression is activated, the LoxP sites undergo recombination to excise the FHIT coding region, resulting in Fhit-deficient tissues.

For activation of FHIT expression in a selected tissue and or at a particular stage of development, the regions of homology in the targeting construct are promoter sequences, comprising insertion fragment which contains multiple stop codons in all reading frames flanked by LoxP sites. Upon insertion of this targeting construct into the FHIT promoter, no FHIT protein is produced. The resulting transgenic animal is crossed to another transgenic animal in which the Cre recombinase is expressed under the control of a spatially and/or temporally regulated promoter. When Cre expression is activated, the LoxP sites undergo recombination to excise the stop codons and restore the FHIT gene to its undisrupted state.

For inducible FHIT activation or inactivation, the Tet operator can replace or be inserted iton the native FHIT regulatory elements, so that the FHIT gene falls under the control of the tetracycline-controllable transactivator (tTA) and tetracycline-controllable repressor (TetR), which can only activate or repress transcription, respectively, in the presence of tetracycline. Transgenic animals comprising the Tet promoter in the FHIT gene are then crossed to animals which express rTA or TetR, constitutively for example, and FHIT expression induced or repressed by administering tetracycline to the animals. Alternatively, cultured cells from the transgenic animals can be produced, the cells transfected with a rTA or TetR expression construct, and the culture contacted with tetracycline to induce or inhibit FHIT expression. For further details, see U.S. Pat. No. 5,922,927.

5.6 Precursor Cells

The specific nonhuman animal cell which is mutated in the present invention is not critical; however, it is preferably a precursor cell or at least pluripotent cell. The term precursor means that the pluripotent cell is a precursor of the desired transfected pluripotent cell of the present invention. Using established techniques, pluripotent cells may be cultured in vivo to form a mutant animal (Evans et al., 1981, Nature 292:292–156).

Wherein the cell which is mutated is a murine cell, examples of murine cells that may be employed in the present invention include, but are not limited to, embryonic stem (ES) cells (preferably primary isolates of ES cells), such as RW4, AB 1 (an hrpt⁻ cell line) or AB 2.1 (AB 1, an hprt⁺ cell line).

Primary isolates of ES cells may be obtained directly from embryos, essentially as described for the EK.CCE cell line or for ES cells in general. The particular embryonic stem cell employed in the present invention is not critical.

ES cells are preferably cultured on stromal cells, e.g., STO cells and/or primary embryonic fibroblast cells as described by Robertson, 1987, In "Teratocarcinomas and embryonic stem cells: a practical approach", E. J. Robertson, ed. (Oxford: IRL Press), pp. 71–112. The stromal (and/or fibroblast) cells serve to reduce the clonal outgrowth of abnormal ES cells.

ES cells harboring a mutant FHIT gene, such as a FHIT gene comprising a substitution mutation resulting in an in-frame stop codon, may be selected in several ways. First, a selectable marker (e.g., neo, gpt, tk) may be linked to the heterologous FHIT gene (e.g., in an intron or flanking sequence) in the targeting construct so that cells having a replacement allele may be selected for. Most usually, a FHIT gene targeting construct will comprise both a positive selection expression cassette and a negative selection expression cassette, so that homologously targeted cells can be selected for with a positive-negative selection scheme. (Mansour et al., 1988, Nature 336: 348). Generally, a positive selection expression cassette is positioned in an intron region of the heterologous FHIT gene replacement region, while a negative selection expression cassette is positioned distal to a homology clamp, such that double-crossover homologous recombination will result in the integration of the positive selection cassette and the loss of the negative selection cassette.

In other embodiments, introduction of the targeting constructs is achieved by pronuclear injection. The preferred precursor cell type for pronuclear injection is a fertilized oocyte.

5.7 Targeting Constructs

Several gene targeting techniques have been described, including but not limited to: co-electroporation, "hit-and-run", single-crossover integration, and double-crossover recombination (Bradley et al., 1992, BioTechnology 10: 534. The invention can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example and not limitation, a preferred embodiment is a targeting construct comprising, in order: (1) a first homology clamp having a sequence substantially identical to a sequence within about 3 kilobases upstream (i.e., in the direction opposite to the translational reading frame of the FHIT gene exons) of an exon of an endogenous FHIT gene, (2) a replacement region comprising a positive selection cassette having a pgk promoter driving transcription of a neo gene, (3) a second homology clamp having a sequence substantially identical to a sequence within about 3 kilobases downstream of said exon of said endogenous FHIT gene, and (4) a negative selection cassette, comprising a HSV tk promoter driving transcription of an HSV tk gene. Such a targeting construct is suitable for double-crossover replacement recombination which deletes a portion of the endogenous FHIT locus spanning said exon and replaces it with the replacement region having the positive selection cassette. If the deleted exon is essential for expression of a functional FHIT gene product, the resultant exon-depleted allele is functionally disrupted and is termed a null allele.

Targeting constructs of the invention comprise at least one homology clamp linked in polynucleotide linkage (i.e., by phosphodiester bonds) to a targeting region. A homology clamp has a sequence which substantially corresponds to, or is substantially complementary to, a predetermined endogenous FHIT gene sequence of a nonhuman host animal, and may comprise sequences flanking the predetermined FHIT gene.

Although no lower or upper size boundaries for recombinogenic homology clamps for gene targeting have been conclusively determined in the art, the best mode for homology clamps is believed to be in the range between about 50 basepairs and several tens of kilobases. Consequently, targeting constructs are generally at least about 50 to 100 nucleotides long, preferably at least about 250 to 500 nucleotides long, more preferably at least about 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred, with one preferred embodiment having a first homology region of about 7 kilobases flanking one side of a replacement region and a second homology region of about 1 kilobase flanking the other side of said replacement region. The length of homology (i.e., substantial identity) for a homology region may be selected at the discretion of the practitioner on the basis of the sequence composition and complexity of the predetermined endogenous FHIT gene target sequence(s) and guidance provided in the art (Hasty et al., 1991, Mol. Cell. Biol. 11: 5586; Shulman et al., 1990, Mol. Cell. Biol. 10: 4466). Targeting constructs have at least one homology region having a sequence that substantially corresponds to, or is substantially complementary to, a predetermined endogenous FHIT gene sequence (e.g., an exon sequence, an enhancer, a promoter, an intronic sequence, or a flanking sequence within about 3–20 kb of a FHIT gene), such as a FHIT gene sequence. Such a targeting transgene homology region serves as a template for homologous pairing and recombination with substantially identical endogenous FHIT gene sequence(s). In targeting constructs, such homology regions typically flank the replacement region, which is a region of the targeting construct that is to undergo replacement with the targeted endogenous FHIT gene sequence (Berinstein et al., 1992, Mol. Cell. Biol. 12: 360, which is incorporated herein by reference). Thus, a segment of the targeting construct flanked by homology regions can replace a segment of an endogenous FHIT gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Without wishing to be bound by any particular theory of homologous recombination or gene conversion, it is believed that in such a double-crossover replacement recombination, a first homologous recombination (e.g., strand exchange, strand pairing, strand scission, strand ligation) between a first targeting construct homology region and a first endogenous FHIT gene sequence is accompanied by a second homologous recombination between a second targeting construct homology region and a second endogenous FHIT gene sequence, thereby resulting in the portion of the targeting construct that was located between the two homology regions replacing the portion of the endogenous FHIT gene that was located between the first and second endogenous FHIT gene sequences. For this reason, homology regions are generally used in the same orientation (i.e., the upstream direction is the same for each homology region of a transgene to avoid rearrangements). Double-crossover replacement recombination thus can be used to delete a portion of an endogenous FHIT gene and concomitantly transfer a nonhomologous portion (e.g., a neo gene expression cassette) into the corresponding chromosomal location. Double-crossover recombination can also be used to add a nonhomologous portion into an endogenous FHIT gene without deleting endogenous chromosomal portions.

However, double-crossover recombination can also be employed simply to delete a portion of an endogenous gene sequence without transferring a nonhomologous portion into the endogenous FHIT gene (see Jasin et al., 1988, Genes Devel. 2:1353). Upstream and/or downstream from the nonhomologous portion may be a gene which provides for identification of whether a double-crossover homologous recombination has occurred; such a gene is typically the HSV tk gene which may be used for negative selection.

Typically, targeting constructs of the invention are used for functionally disrupting endogenous FHIT genes and comprise at least two homology regions separated by a nonhomologous sequence which contains an expression cassette encoding a selectable marker, such as neo (Smith and Berg, 1984, Cold Spring Harbor Symp. Quant. Biol. 49: 171; Sedivy and Sharp, 1989, Proc. Natl. Acad. Sci. (U.S.A.) 86: 227; Thomas and Capecchi, 1987, cell 51:503, which are incorporated herein by reference). However, some targeting transgenes of the invention may have the homology region (s) flanking only one side of a nonhomologous sequence. Targeting transgenes of the invention may also be of the type referred to in the art as "hit-and-run" or "in-and-out" transgenes (Valancius and Smithies, 1991, Mol. Cell. Biol. 11: 1402; Donehower et al. (1992) Nature 356: 215; (1991) J. NIH Res. 3: 59; which are incorporated herein by reference).

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker. Selectable markers typically are also be used for hit-and-run targeting constructs and selection schemes (Valancius and Smithies, 1991, Mol. Cell. Biol. 11: 1402.

An expression cassette typically comprises a promoter which is operational in the targeted host cell (e.g., ES cell) linked to a structural sequence that encodes a protein or polypeptide that confers a selectable phenotype on the targeted host cell, and a polyadenylation signal. A promoter included in an expression cassette may be constitutive, cell type-specific, stage-specific, and/or modulatable (e.g., by hormones such as glucocorticoids; MMTV promoter), but is expressed prior to and/or during selection. An expression cassette can optionally include one or more enhancers, typically linked upstream of the promoter and within about 3–10 kilobases. However, when homologous recombination at the targeted endogenous site(s) places the nonhomologous sequence downstream of a functional endogenous promoter, it may be possible for the targeting construct replacement region to comprise only a structural sequence encoding the selectable marker, and rely upon the endogenous promoter to drive transcription (Doetschman et al., 1988, Proc. Natl. Acad. Sci. (U.S.A.) 85: 8583. Similarly, an endogenous enhancer located near the targeted endogenous site may be relied on to enhance transcription of transgene sequences in enhancerless transgene constructs. Preferred expression cassettes of the invention encode and express a selectable drug resistance marker and/or a HSV thymidine kinase enzyme. Suitable drug resistance genes include, for example: gpt (xanthine-guanine phosphoribosyltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg (1981) Proc. Natl. Acad. Sci. (U.S.A.) 78: 2072; Southern and Berg (1982) J. Mol. Appl. Genet. 1: 327; which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it would integrate only by nonhomologous recombination. Such positioning generally is accomplished by linking the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location. A nucleoside analog, gancyclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme can be used (Mansour et al., 1988, Nature 366: 348. Positive-negative selection involves the use of two active selection cassettes: (1) a positive one (e.g., the neo gene), that can be stably expressed following either random integration or homologous targeting, and (2) a negative one (e.g., the HSV tk gene), that can only be stably expressed following random integration, and cannot be expressed after correctly targeted double-crossover homologous recombination. By combining both positive and negative selection steps, host cells having the correctly targeted homologous recombination between the transgene and the endogenous FHIT gene can be obtained.

Figure 4:

Generally, targeting constructs of the invention preferably include: (1) a positive selection expression cassette flanked by two homology regions that are substantially identical to host cell endogenous FHIT gene sequences, and (2) a distal negative selection expression cassette. However, targeting constructs which include only a positive selection expression cassette can also be used. Typically, a targeting construct will contain a positive selection expression cassette which includes a neo gene linked downstream (i.e., towards the carboxy-terminus of the encoded polypeptide in translational reading frame orientation) of a promoter such as the HSV tk promoter or the pgk promoter. More typically, the targeting transgene will also contain a negative selection expression cassette which includes an HSV tk gene linked downstream of a HSV tk promoter. For example, but not to limit the invention, a schematic representation of a typical positive-negative FHIT targeting construct of the invention is shown in FIG. 4.

It is preferred that targeting constructs of the invention have homology regions that are highly homologous to the predetermined target endogenous DNA sequence(s), preferably isogenic (i.e., identical sequence). Isogenic or nearly isogenic sequences may be obtained by genomic cloning or high-fidelity PCR amplification of genomic DNA from the strain of nonhuman animals which are the source of the ES cells used in the gene targeting procedure. Typically, targeting polynucleotides of the invention have at least one homology region that is at least about 50 nucleotides long, and it is preferable that homology regions are at least about 75 to 100 nucleotides long, and more preferably at least about 200–2000 nucleotides long, although the degree of sequence homology between the homology region and the targeted sequence and the base composition of the targeted sequence will determine the optimal and minimal homology region lengths (e.g., G-C rich sequences are typically more thermodynamically stable and will generally require shorter homology region length). Therefore, both homology region length and the degree of sequence homology can only be determined with reference to a particular predetermined sequence, but homology regions generally must be at least about 50 nucleotides long and must also substantially correspond or be substantially complementary to a predetermined endogenous target sequence. Preferably, a homology region is at least about 100 nucleotides long and is identical to or complementary to a predetermined target sequence in or flanking a FHIT gene. If it is desired that correctly targeted homologous recombinants are generated at high efficiency, it is preferable that at least one homology region is isogenic (i.e., has exact sequence identity with the crossover target sequence(s) of the endogenous FHIT gene), and is more preferred that isogenic homology regions flank the exogenous targeting construct sequence that is to replace the targeted endogenous FHIT sequence.

Generally, any predetermined endogenous FHIT locus can be altered by homologous recombination (which includes gene conversion) with an targeting transgene that has at least one homology region which substantially corresponds to or is substantially complementary to a predetermined endogenous FHIT gene locus sequence in a mammalian cell having said predetermined endogenous FHIT gene sequence. Typically, a targeting transgene comprises a portion having a sequence that is not present in the preselected endogenous targeted FHIT sequence(s) (i.e., a nonhomologous portion) which may be as small as a single mismatched nucleotide or may span up to about several kilobases or more of nonhomologous sequence. Generally, such nonhomologous portions are flanked on each side by homology regions, although a single flanking homology region may be used (e.g., in insertion transgenes). Nonhomologous portions are used to make insertions, deletions, and/or replacements in a predetermined endogenous targeted FHIT gene sequence, and/or to make single or multiple nucleotide substitutions in a predetermined endogenous target DNA sequence so that the resultant recombined sequence (i.e., a functionally disrupted endogenous FHIT gene) incorporates the sequence information of the nonhomologous portion of the targeting construct(s). Substitutions, additions, and deletions may be as small as 1 nucleotide or may range up to about 2 to 10 kilobases or more. A preferred nonhomologous portion of a targeting transgene is a selectable drug resistance marker (e.g., the neo gene), which may be transferred to a chromosomal location, stably replicated, and selected for with a selection agent (e.g., G418). Targeting transgenes can be used to inactivate one or more FHIT genes in a cell, such as in a murine ES cell, and transgenic nonhuman animals harboring such inactivated genes may be produced.

Once the specific FHIT gene(s) to be modified are selected, their sequences will be scanned for possible disruption sites (e.g., a segment of the murine FHIT gene spanning the second and third exons). Plasmids are engineered to contain an appropriately sized construct replacement sequence with a deletion or insertion in the FHIT gene of interest and at least one flanking homology region which substantially corresponds or is substantially complementary to an endogenous target DNA sequence. Typically two flanking homology regions are used, one on each side of the replacement region sequence. For example, but not to limit the invention, one homology region may be substantially identical to a sequence upstream (i.e., the direction towards the transcription start site(s) of the murine FHIT second exon and a second homology region may be substantially identical to a sequence downstream of the murine FHIT third exon. A preferred method of the invention is to transfer a targeting transgene into a pluripotent stem cell line which can be used to generate transgenic nonhuman animals following injection into a host blastocyst. A particularly preferred embodiment of the invention is a FHIT gene targeting construct containing both positive (e.g., neo) and, optionally, negative (e.g., HSV tk) selection expression cassettes. The FHIT targeting transgene is transferred into mouse ES cells (e.g., by electroporation) under conditions suitable for the continued viability of the electroporated ES cells. The electroporated ES cells are cultured under selective conditions for positive selection (e.g., a selective concentration of G418), and optionally are cultured under selective conditions for negative selection (e.g., a selective concentration of gancyclovir or FIAU), either simultaneously or sequentially. Selected cells are then verified as having the correctly targeted transgene recombination by PCR analysis according to standard PCR or Southern blotting methods known in the art (U.S. Pat. No. 4,683,202; Erlich et al., 1991, Science 252: 1643. Correctly targeted ES cells are then transferred into suitable blastocyst hosts for generation of chimeric transgenic animals according to methods known in the art (Capecchi, M., 1989, Trends Genet. 5: 70.

Briefly, the invention involves the inactivation of an FHIT gene, most usually a FHIT gene, by homologous recombination in a pluripotent cell line that is capable of differentiating into germ cell tissue. A DNA construct that contains an altered, copy of a mouse FHIT gene (e.g., a FHIT gene) is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells derived from the mutant cell line. Therefore, by breeding the chimeric mice it is possible to obtain a new line of mice containing the introduced genetic lesion (reviewed by Capecchi, M., 1989, Trends Genet. 5: 70.

To disrupt the murine FHIT gene, a targeting construct based on the design employed by Jaenisch and co-workers (Zjilstra, et al., 1989, Nature 342: 435–438 for the successful disruption of the mouse β2-microglobulin gene can be used. The neomycin resistance gene (neo), from the plasmid pMCINEO is inserted into the coding region of the target FHIT gene. The pMCIneo insert uses a hybrid viral promoter/enhancer sequence to drive neo expression. This promoter is active in embryonic stem cells. Therefore, neo can be used as a selectable marker for integration of the targeting construct. The HSV thymidine kinase (tk) gene is added to the end of the construct as a negative selection marker against random insertion events (Zjilstra et al., 1989, Nature 342: 435–438.

Vectors containing a targeting construct are typically grown in E. coli and then isolated using standard molecular biology methods, or may be synthesized as oligonucleotides. Direct targeted inactivation which does not require prokaryotic or eukaryotic vectors may also be done. Targeting transgenes can be transferred to host cells by any suitable technique, including microinjection, electroporation, lipofection, biolistics, calcium phosphate precipitation, and viral-based vectors, among others. Other methods used to transform mammalian cells include the use of Polybrene, protoplast fusion, and others (see, generally, Sambrook et al. Molecular Cloning: A Laboratory Manual., 2d ed., 1989, Cold Spring Harbor Laboratory Press, Cold Spring Harbor, N.Y.

It is preferable to use a transfection technique with linearized transgenes containing only modified target gene sequence(s) and without vector sequences. The modified gene site is such that a homologous recombinant between the exogenous targeting construct and the endogenous DNA target sequence can be identified by using carefully chosen primers and PCR or by Southern blot analysis, followed by analysis to detect if PCR products or Southern blot bands specific to the desired targeted event are present (Erlich et al., 1991, Science 252: 1643. For example, as described in Section 6.2 below and in FIG. 1, a targeted disruption of the murine FHIT locus gives rise to an 8.7 kb BamH1 fragment, in contrast with its 5 kb wild-type counterpart. Southern blot analysis of genomic DNA digested with BamH1 can identify the differences. In addition, as shown in FIG. 1, a targeted locus can be identified by virtue of a change in size of a given PCR product (for example, amplification of genomic DNA with primers F and R produces fragments of different lengths in targeted and non-targeted cells), or the production of a PCR product from the genome of the targeted cell that is not amplifiable in non-targeted cells (e.g., by amplification of genomic DNA with primers N and R).

Several studies have already used PCR to successfully identify the desired transfected cell lines (Zimmer and Gruss, 1989, Nature 338: 150; Mouellic et al., 1990, Proc. Natl. Acad. Sci. (U.S.A.) 87: 4712; Shesely et al., 1991, Proc. Natl. Acad. Sci. USA 88: 4294. This approach is very effective when the number of cells receiving exogenous targeting transgene(s) is high (i.e., with electroporation or with liposomes) and the treated cell populations are allowed to expand (Capecchi, 1989, Trends Genet. 5:70).

For making transgenic non-human animals (which include homologously targeted non-human animals), embryonic stem cells (ES cells) are preferred. Embryonic stem cells are manipulated according to published procedures (Teratocarcinomas and Embryonic Stem Cells: A Practical Approach, E. J. Robertson, ed., IRL Press, Washington, D.C., 1987; Zjilstra et al., Nature 342: 435–438, 1989; and Schwartzberg et al., 1989, Science 246: 799–803.

Wherein the transgenic nonhuman animal is a mouse, murine ES cells are used, such as AB-1 line grown on mitotically inactive SNL76/7 cell feeder layers (McMahon and Bradley, 1990, Cell 62:1073–1085). Other suitable ES lines include, but are not limited to, the E14 line (Hooper et al., 1987, Nature 326: 292–295), the D3 line (Doetschman et al., 1985, J. Embryol. Exp. Morph. 87: 27–45), and the CCE line (Robertson et al., 1986, Nature 323: 445–448). In a preferred embodiment the ES cell line is RW4 (Gnome Systems).

The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having an inactivated endogenous FHIT loci and are backcrossed and screened for the presence of the correctly targeted transgene(s) by PCR or Southern blot analysis on tail biopsy DNA of offspring so as to identify transgenic mice heterozygous for the inactivated FHIT locus/loci. By performing the appropriate crosses, it is possible to produce a transgenic nonhuman animal homozygous for a disrupted FHIT locus. Fhit-deficient animals may also be crossed to mice carrying other mutations, such as Msh2-deficient mice (U.S. Pat. No. 5,907,079).

5.8 Generation of Fhit-Deficient Mice

Most usually, a targeting construct is transferred by electroporation or microinjection into a totipotent embryonal stem (ES) cell line, such as the murine RW4, AB-1 or CCE lines. The targeting construct homologously recombines with endogenous sequences in or flanking a FHIT gene locus and functionally disrupts at least one allele of the FHIT gene. Typically, homologous recombination of the targeting construct with endogenous FHIT locus sequences results in integration of a nonhomologous sequence encoding and expressing a selectable marker, such as neo, usually in the form of a positive selection cassette (infra). The functionally disrupted allele is termed a FHIT null allele. ES cells having at least one FHIT null allele are selected for by propagating the cells in a medium that permits the preferential propagation of cells expressing the selectable marker. Selected ES cells are examined by PCR analysis and/or Southern blot analysis to verify the presence of a correctly targeted FHIT allele.

In order to obtain the FHIT deficient mice of the present invention, the mutant embryonic stems cells are injected into mouse blastocysts as described by Bradley, 1987, In "Teratocarcinomas and embryonic stem cells: a practical approach", E. Robertson, ed. (Oxford: IRL Press), pp. 113–151. The particular mouse blastocysts employed in the present invention are not critical. Examples of such blastocysts include those derived from C57BL6 mice, C57BL6Albino, Swiss outbred, CFLP, MFI, and the like. Chimeric targeted mice are derived according to Hogan, et al., Manipulating the Mouse Embryo: A Laboratory Manual., Cold Spring Harbor Laboratory, 1988; and Teratocarcinomas and Embryonic Stem Cells: A Practical Approach, E. J. Robertson, ed., IRL Press, Washington, D.C., 1987.

Breeding of nonhuman animals which are heterozygous for a null allele may be performed to produce nonhuman animals homozygous for said null allele, so-called "knockout" animals (Donehower et a., 1992, Nature 256: 215; Travis, 1992, Science 256: 1392. Alternatively, ES cells homozygous for a null allele having an integrated selectable marker can be produced in culture by selection in a medium containing high levels of the selection agent (e.g., G418 or hygromycin). Heterozygosity and/or homozygosity for a correctly targeted null allele can be verified with PCR analysis and/or Southern blot analysis of DNA isolated from an aliquot of a selected ES cell clone and/or from tail biopsies.

In alternative embodiments, the targeting construct is introduced into the germline of a nonhuman animal by other methods, e.g., by pronuclear injection of recombinant genes into pronuclei of one-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082,779; 5,304,489; 5,174,986; 5,175,384; 5,175,385; 5,221,778; Gordon et al., 1980, Proc. Natl. Acad. Sci. 77:7380–7384; Palmiter et al., 1985, Cell 41:343–345 (1985); Palmiter et al., 1986, Ann. Rev. Genet, 20:465–499; Askew et al., 1993, Mol. Cell. Bio., 13:4115–4124; Games et al., 1995, Nature, 373:523–527; Valancius and Smithies, 1991, Mol. Cell. Bio., 11:1402–1408; Stacey et al., Mol. Cell. Bio., 1994, 14:1009–1016; Hasty et al., 1995, Nature, 350:243–246; Rubinstein et al., 1993, Nucl. Acid Res., 21:2613–2617.

The mutant mice of the present invention may be intercrossed to obtain embryos homozygous for the mutation in the FHIT gene, and/or may be crossed with other mice strains to transfer the Fhit mutation into these other strains. In one embodiment, Fhit mutant mice are crossed to MSH2 mutant mice.

5.9 Assaying FHIT Expression or Activity in Fhit-Deficient Mice

The extent of Fhit deficiency can easily be measured by using standard molecular biology methods. For instance, one can measure for a deficiency in FHIT messenger RNA levels by using reverse transcriptase mediated polymerase chain reaction (RT-PCR).

In other embodiments, the extent of Fhit deficiency in a Fhit-deficient animal of the invention can be assayed by measuring protein levels or activity by various methods. For example, in one embodiment, protein extracts from Fhit-deficient cells and tissues are assayed for their levels of FHIT protein by ability to various immunoassays known in the art. Such immunoassays include but are not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one mode of the embodiment, antibody binding is detected by detecting a label on the primary antibody. In another mode of embodiment, the primary antibody is detected by detecting binding of a secondary antibody or reagent to the primary antibody. Optionally, the secondary antibody can be labeled. Many means are known in the art for detecting binding in an immunoassay and are within the scope of the present invention.

For the purposes of the present invention, a cell or animal that has been engineered to be FHIT deficient shall generally express at least about 20 percent less FHIT than a corresponding wild type cell or animal, and preferably at least about 50 percent less FHIT than a corresponding wild type cells or animals. In other embodiments, a cell or animal that is FHIT deficient expresses at least about 90 percent less FHIT than a corresponding wild type cell or animal, more preferably less than 1.0 percent of the FHIT protein found in wild type cells or animals, and in a specifically preferred embodiment the Fhit deficient cells or animals will produce undetectable levels of full-length (wild type) FHIT transcript.

5.10 Drug Screening Assays

As shown in section 6, infra, Fhit-deficient animals are predisposed to developing diseases or disorders involving cell overproliferation (e.g., malignancy). In particular, Fhit-deficient mice developed sebaceous and visceral tumors reminiscent of those seen in humans with Muir-Torre Syndrome. The mice are of use as animal models of Muir-Torre Sybdrome e.g., to screen for or test molecules (e.g., potential anti-cancer therapeutics) for the ability to inhibit overproliferation (e.g., tumor formation) and thus treat or prevent such diseases or disorders. Of particular interest are screening assays for agents that have a low toxicity for human cells.

A wide variety of assays may be used for this purpose, such as those described below. Depending on the particular assay, whole animals may be used, or cells derived therefrom. Cells may be freshly isolated from an animal, or may be immortalized in culture. Cells of particular interest include visceral and sebaceous tissues of the transgenic animals of the invention, and cultures derived therefrom.

The term "agent" as used herein describes any molecule, e.g. protein or non-protein organic pharmaceutical, with the capability of affecting any aspect of the biological actions of FHIT activity. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon on heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modelling.

Screening may be directed to known pharmacologically active compounds and chemical analogs thereof, or to new agents with unknown properties such as those created through rational drug design. Candidate agents for arresting and/or reversing tumor growth may be used.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The insoluble supports may be any compositions to which polypeptides can be bound, which is readily separated from soluble material, and which is otherwise compatible with the overall method. The surface of such supports may be solid or porous and of any convenient shape. Examples, of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

A number of assays are known in the art for determining the effects of a test molecule on cancer cells. Such assays may use cells of a cancer cell line, e.g., a cell line derived from a Fhit mutant mouse. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies are from Santa Cruz Inc.). mRNA can be quantitated by methods that are well known and routine in the art, for example by Northern analysis, RNase protection, the polymerase chain reaction in connection with the reverse transcription, etc. Cell viability can be assessed by using trypan-blue staining or other cell death or viability markers known in the art. Differentiation can be assessed visually based on changes in morphology, etc.

The present invention provides methods for screening of inhibitors of the proliferation Fhit mutant cells by a variety of techniques known in the art, including but not limited to the following methods of measuring cellular proliferation:

As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., 1986, Int. J. Cancer 38, 369; Campana et al., 1988, J. Immunol. Meth. 107, 79).

Cell proliferation may also be examined using ($^3$H)-thymidine incorporation (see e.g., Chen, J., 1996, Oncogene 13:1395–403; Jeoung, J., 1995, J. Biol. Chem. 270:18367–73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189–199; Vassilev et al., 1995, J. Cell Sci. 108:1205–15).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidium iodide assay (see e.g. Turner, T., et al., 1998, Prostate 34:175–81). Alternatively, the DNA ploidy may be determined by quantitation of DNA Feulgen staining (which binds to DNA in a stoichiometric manner) on a computerized microdensitometrystaining system (see e.g., Bacus, S., 1989, Am. J. Pathol.135:783–92). In an another embodiment, DNA content may be analyzed by preparation of a chromosomal spread (Zabalou, S., 1994, Hereditas.120:127–40; Pardue, 1994, Meth. Cell Biol. 44:333–351).

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{cip1}$. Increased levels of p21 expression in cells results in delayed entry into G1 of the cell cycle (Harper et al., 1993, Cell 75:805–816; Li et al., 1996, Curr. Biol. 6:189–199). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell cycle or speed of cell cycle may also be used to measure inhibition of Fhit mutant cell proliferation by test molecules. In one embodiment the length of the cell cycle is determined by the doubling time of a population of cells (e.g., using cells contacted or not contacted with one or more test compounds). In another embodiment, FACS analysis is used to analyze the phase of cell cycle progression, or purify G1, S, and G2/M fractions (see e.g., Delia, D. et al., 1997, Oncogene 14:2137–47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weinert, T., and Hartwell, L., 1993, Genetics, 134:63–80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

In addition to the effects of expression of a particular cell cycle protein, activity and post-translational modifications of proteins involved in the cell cycle can play an integral role in the regulation and proliferative state of a cell. The invention provides for assays involved detected post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., 1988, Biochem. J. 250:485–91; Paige, L., 1988, Biochem J.;250:485–91).

Activity of signaling and cell cycle proteins and/or protein complexes is often mediated by a kinase activity. The present invention provides for analysis of kinase activity by assays such as the histone H1 assay (see e.g., Delia, D. et al., 1997, Oncogene 14:2137–47).

To test the ability of a test compound to inhibit tumor development in Fhit deficient cells, the compound can also be demonstrated to inhibit cell transformation (or progression to malignant phenotype) in vitro. In this embodiment Fhit deficient cells with a transformed cell phenotype are contacted with one or more test compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436–446).

Loss of invasiveness or increased adhesion may also be used to demonstrate the anti-cancer effects of a test compound on Fhit deficient cells. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., 1997, Science 278:1464–66).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells and may be used to test the invasiveness of other neoplastic cell types. This assay identifies a cell population that has lost cell scattering activity in response to HGF (Hordijk et al., 1997, Science 278:1464–66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., 1993, Biochem. Biophys. Res. Commun.193:518–25).

For example, lead compound identified by the in vitro screening methods described herein can be administered to a Fhit deficient or null mouse and the mouse subsequently examined for a decreased incidence of visceral and/or sebaceous tumor formation in comparison with controls not administered the lead compound. Alternatively, lead compound can be administered to a Fhit deficient or null mouse that has developed tumors and subsequently examining the tumors in the mouse for tumor regression in comparison to controls not administered the lead compound.

Lead compounds can then be demonstrated to inhibit tumor formation in vivo.

Preferably, the screen will include control values (e.g., the incidence of tumors in the test animal or the rate of proliferation in culture and cancerous cells derived from the test animal in the absence of test compound(s)). Test substances which are considered positive, i.e., inhibit tumor growth in vivo or cell proliferation in vitro, are likely to be beneficial in the treatment of Muir-Torre associated cancers, and will be considered useful lead candidates for drug development.

5.11 Carcinogenicity Testing

The transgenic animals of the present invention and cells cultured therefrom can be used to assay the carcinogenicity of a test agent according to standard methods known in the art. Such methods include but are not limited the method described in Section 6.1, infra, and those described in DiPaolo et al., 1969, J. Natl. Cancer Inst. 42:867; Reznikoff, et al., 1973, Cancer Res. 33:3231; Kakunaga, 1973, Intl. J. Cancer, 12:463; U.S. Pat. No. 4,753,874; U.S. Pat. No. 5,273,880; U.S. Pat. No. 4,885,238; U.S. Pat. No. 4,302,535; U.S. Pat. No. 5,506,131; U.S. Pat. No. 5,429,948; and U.S. Pat. No. 5,180,666. The agent suspected to be a carcinogen may be a molecule, for example a chemical carcinogen, ionizing radiation, or an electromagnetic field. The carcinogen may also be capable of inducing free radical formation.

In a specific embodiment, assaying the carcinogenicity of a test molecule is done according to the methods of U.S. Pat. No. 6,020,146, which discloses an in vitro method comprising exposing a cell sample to a test molecule for a period of time up to about seven days, agglomerating the cell sample, administrating a halogenated deoxyuridine analog (which is incorporated by cells transformed by a carcinogen and is not incorporated by untransformed spheroid cells) and a thymidilate synthetase inhibitor to the agglomerated cell sample, and dispersing the agglomerated cell sample on a growth surface of a culture vessel. The cell sample is then contacted with an antibody which specifically binds to the halogenated deoxyuridine and the amount of antibody binding is detected and quantitated by standard immunoassay. A test compound is said to be a carcinogen if the amount of halogenated deoxyuridine is at least twice as much in cells contacted with the test molecule as cells not contacted with the test molecule.

In another specific embodiment, the carcinogenicity of a test molecule is correlated with the level of tyrosylphosphorylated cyclin dependent kinase (CDK), such as $p34^{cdc2}$, according to the method of U.S. Pat. No. 5,955,289.

In yet another specific embodiment, tissue-specific carcinogenicity (e.g. carcinogenicity towards sebaceous tissue versus hepatic tissue) of a test compound is measured, for example as described in U.S. Pat. No. 5,925,524.

Optionally, a test molecule is incubated with liver extracts prior to its exposure to the Fhit-deficient animal or cell, in order to test the molecule as may be chemically altered by the liver (Ames et al., 1975, Mut. Res. 31:347–364).

For whole-animal testing, the test compound suspected of having carcinogenic activity is introduced into the animal by any suitable method, including but not limited to injection, or ingestion or topical administration.

Alternative embodiments for implementing the methods and producing the cells and animals of the present invention will be apparent to one of skill in the art and are intended to be comprehended within the accompanying claims. The following experimental examples are offered by way of illustration and not by way of limitation.

6. EXAMPLES

6.1 Materials and Methods
Immunoblot Analysis of Murine Fhit Protein

A glutathione S-transferase (GST) gene-fused murine FHIT cDNA recombinant was cloned into a bacterial expression vector. In the resulting construct, pGEX4T1-mFhit, the murine Fhit protein coding sequence was placed downstream of the GST gene. GST-mFhit fusion protein was produced in the BL21 bacterial strain (Druck et al., 1977, Cancer Res. 57:504–512), and after purification GST-mFhit was cleaved with thrombin protease. Polyclonal antiserum against purified mouse Fhit protein was raised commercially (Cocalico Biologicals, Reamstown, Pa.) and used at 1:8000 dilution in immunoblot and 1:4000 in immunohistochemistry experiments. Specificity was tested on protein lysates from murine cells and tissues with and without endogenous or exogenous Fhit protein expression.

Immunohistochemistry

After antigen retrieval endogenous peroxidase was inhibited with 3% hydrogen peroxide, and nonspecific binding sites were blocked with normal goat serum (Fong et al., 1997, Carcinogenesis 18:1477–1484). Slides were incubated with primary rabbit anti-murine Fhit (1:4000 dilution, overnight), followed by incubation with biotinylated goat anti-rabbit antibody. Slides were then incubated with strepavidin horseradish peroxidase (Dako, 1:1000 dilution). Fhit protein was localized by a final incubation with 3,3'-diaminobenzidine tetrahydrochloride (DAB, Sigma). Slides were counterstained with hematoxylin, dehydrated and coverslipped.

Carcinogenicity Study (C57BL/6J X 129/SvJ) F1 mice (B6129F1s) that were Fhit +/+ or +/− were produced. 18 Fhit +/+ and 22 Fhit +/− mice (30–46 weeks) were given 8 intragastric doses of NMBA (Ash Stevens, Detroit, Mich.) over the course of 3 weeks at 2 mg/kg body weight. About half the mice were sacrificed six weeks after the final NMBA dose and the remaining mice at ten weeks. Tumor incidence differences were analyzed by two-tailed Fisher's exact test (Armitage and Berry, 1987, Statistical Methods in Medical Research, $2^{nd}$ Ed., Blackwell Scientific, Oxford). For comparison, four untreated Fhit +/− mice (54–59 weeks old) and one untreated Fhit +/+ mouse (59 weeks old) were similarly autopsied. At autopsy, whole esophagi and stomachs were removed and opened longitudinally. Other tissues with apparent tumors were also examined. The number of animals bearing tumors in the esophagus, forestomach, squamocolumnar junction with the glandular stomach (SCJ) and other tissues were scored. Tissues were fixed in buffered formalin and examined histologically after hematoxylin and eosin (H&E) staining for the presence of hyperkeratosis, parakeratosis, dysplasia, papillomas, adenomas and carcinomas.

MTS Cases

Archival paraffin blocks for two cases of MTS were available from the Surgical Pathology archives of Thomas Jefferson University Hospital (case 1) and the Christiana Hospital (case 2). For case 1, paraffin blocks for two sebaceous tumors were available, and for case 2 one sebaceous tumor block. Normal and tumor cells were microdissected from the paraffin blocks and DNA prepared. Tissue sections were analysed for Fhit expression by immunohistochemistry as described (Hadaczek et al., 1998, Cancer Res. 58:2946–2951). Germline DNA was prepared from peripheral blood lymphocytes of the MTS patients.

Microsatellite Instability Analysis (MSI)

Portions of the large sebaceous tumors were lysed in buffer containing 0.6% SDS and 50 µg/ml proteinase K and tumor DNAs prepared by standard phenol-chloroform extraction and ethanol precipitation. MSI was assayed by PCR amplification with primers for D1Mit4, D2Mit13, D3Mit1, D3Mit203, D6Mit59, D8Mit14, D10Mit2, D14Nds1, D17Mit123 and D19Mit36 for murine alleles (Reitmair et al., 1996, Cancer Res. 56:3842–3849) and primers D2S123, D3S1298, D18S35, BAT25 and BAT26 (Kruse et al., 1998, Am. J. Hum. Genet. 63:63–70; Bocker et al., 1997, Cancer Res. 57:4739–4743) for human alleles were purchased from Research Genetics or the Kimmel Cancer Center Nucleic Acid Facility at Thomas Jefferson University. Samples were amplified in a reaction mixture containing 50 ng template DNA, 10 mM Tris-HCl (pH 8.3), 50 mM KCl, 0.1 mg/ml gelatin, 1.5 mM $MgCl_2$, 12.5 µM each dNTP, 0.5 units Taq polymerase, 20 ng primers and 1 µCi [$^{32}$P] dCTP, for 30 cycles of 94° C. for 30s, 57° C. for 30s and 72° C. for 30s. PCR product (1 ml) was mixed with 9 ml sequencing stop buffer (95% formamide, 0.05% bromphenol blue, 0.05% xylene cyanol FF and 10 mM NaOH) and denatured at 94° C. for 8 min. Seven µl of this mixture was loaded onto a 6% acrylamide: bis (19:1), 8 M urea gel for electrophoresis at 80 watts for 2–3 h. The gel was dried and exposed to X-ray film overnight.

Fhit Sequence Analysis

Primer pairs flanking each of the human FHIT exons (Druck et al., 1977, Cancer Res. 57:504–512) and the mouse FHIT coding exons were used in PCR amplification of DNA from MTS cases or mouse tumors, respectively. Primer pairs surrounding the mouse FHIT exons were previously published (Pekarsky et al., 1998, Cancer Res. 58:3401–3408) for exons 5 and 6 or newly designed for

```
exon 4 (mfiex4F:
GTGTTCTTCACAGTTACG      (SEQ. ID. NO.:4),);

mfiex4R:
CAATTCTATACATTCTTTGC    (SEQ. ID. NO.:5), exon 7 (mfiex7F:
GGCCTGCTGGATAATTCATA    (SEQ. ID. NO.:6),;

mfiex7R:
AGATAACATAATGAAAGAGC    (SEQ. ID. NO.:7)), exon 8 (mfiex8F:
CACTGTCAAGTCAAAATATAG   (SEQ. ID. NO.:8),;

mfiex8R(2):
GGCCTTGTGACTAAATAATAA   (SEQ. ID. NO.:9)), and exon 9 (mfiex9F:
CTCTCTCCTCCAATGTTAT     (SEQ. ID. NO.:10),;

mfiex9R:
AAGGTTAGCAGAAAGAGG      (SEQ. ID. NO.:11)).
```

The products were purified with a PCR purification kit (Qiagen) before sequencing using Taq DyeDeoxy Terminator Cycle Sequencing Kits (ABI). Sequencing reaction products were electrophoresed and recorded on a 377 DNA sequencer (ABI).

Southern Blot Analysis

To examine the integrity of the murine Fhit alleles in tumors, DNA from several sebaceous tumors was digested with restriction enzyme XbaI, electrophoresed on 0.8% agarose gels and transferred to nylon membranes. After drying, membrane-bound DNAs were hybridized to $^{32}$P-labeled full-length murine Fhit cDNA or to exons 1–4, 4–10 or 7–9, to determine if portions of Fhit alleles were deleted. Densitometry analysis of specific lanes of Southern blot autoradiographs was performed. Quantitation of signals was performed using ImageQuant software (Molecular Dynamics, Inc. Sunnyvale, Calif.).

6.2 Results

Production of Fhit$^{tm2KCC}$ Mice

A 129/SvJ mouse genomic fragment encompassing Fhit exon 5 was cloned and a termination codon introduced into the exon 5 coding region. Exon 5 is the first protein coding exon, so that the termination codon prevents translation of a protein. There are no downstream Met codons that can initiate translation of a stable protein (Huebner et al., 1998, Ann. Rev. Genet. 32:7–31). This altered genomic clone was inserted into a derivative of the Mc1-TK vector along with the PGK Neo bpa gene (FIG. 1). RW4 ES cells (Genome Systems) were transfected with this Fhit targeting vector and ES cell clones selected with the vector integrated through homologous recombination into an endogenous Fhit allele (FIG. 1). The targeted ES cell clones were introduced into 3.5 day blastocysts to generate chimeras. Each of the chimeras transmitted the defective Fhit allele to offspring, as determined by Southern blot analysis of tail DNA from agouti pups. Progeny from one chimera (+/Fhit$^{tm2KCC}$ referred to as Fhit +/− mice) were intercrossed and genotyping revealed that all three genotypes were represented, with a ratio close to the expected Mendelian distribution Disruption of the Fhit locus in the knockout mice was further verified by PCR analysis, as illustrated in FIG. 1. Results from Southern and PCR analysis confirmed that the Fhit −/− mice do not carry a wild-type Fhit locus. PCR analysis was used in routine typing of pups from the intercross.

To confirm absence of a functional Fhit gene in Fhit −/− mice, weanling mice were sacrificed and organs removed for assessment of Fhit protein expression by immunoblot analysis and immunohistochemistry. Immunoblot analysis showed that Fhit −/− mouse tissues were entirely negative for Fhit protein (FIG. 2); immunohistochemical detection of Fhit protein in Fhit +/+, +/− and −/− kidney sections showed absence of Fhit protein in Fhit −/− sections and reduced expression in Fhit +/− sections.

NMBA Induction of Tumors

At six weeks after the final NMBA dose, there was no visible difference in the Fhit +/+ and +/− mice. By ten weeks after the final dose, three of the Fhit +/− mice showed tumors in the subcutis of the abdomen. On autopsy at 10 weeks, more than 50% of the Fhit +/− mice exhibited one or more of these tumors in the abdominal, mammary or axial area, sometimes invading muscle tissue; the tumors varied in color from yellow to white. The tumors were removed for fixation prior to examination of the esophagus/forestomach. Extragastric tumors were not observed in the Fhit +/+ mice.

On inspection of whole esophagus and stomach tissues at six weeks after treatment, seven of ten Fhit +/− mice showed one or more small tumors, while two of ten Fhit +/+ mice showed a very small tumor of the esophagus or forestomach. At ten weeks, eleven of twelve Fhit +/− mice showed apparent tumors, usually multiple, in the forestomach, the squamocolumnar junction with the hind stomach and/or in other tissues (Table 1); two of eight Fhit +/+ mice exhibited tumors.

An untreated Fhit +/+ mouse (59 weeks) showed no abnormalities of skin, esophagus, forestomach, or junction. Other internal organs appeared normal. Three of four untreated Fhit +/− mice (54–59 wks) showed a small abdominal tumor in the skin and one Fhit +/− mouse showed a slightly enlarged spleen. Otherwise, the four +/− and one +/+ untreated animals were normal and healthy.

Histological and Immunohistochemical Analyses

Esophageal tumors were not observed on autopsy, but histological examination revealed an esophageal squamous papilloma in 1/10 Fhit +/+ mice at six weeks after NMBA and in Fhit +/− mice 33 and 36 at ten weeks post NMBA (Table 1). At six weeks post NMBA treatment Fhit +/− mice had more tumors than Fhit +/+ mice (70% vs 20%; summarized in Table 2). At ten weeks post NMBA treatment the difference between tumor burden in Fhit +/− mice (100%) compared to +/+ mice (25%) was highly significant (Tables 1 and 2). Most of the tumors were in the forestomach and squamocolumnar junction with the glandular stomach, as observed previously in B6 mice (Fong and Magee, 1999, Cancer Letters 143:63–69). Histological examination of the abdominal tumors of the Fhit +/− mice showed that they derived from sebaceous glands (Table 1, FIG. 3) and were identical to the sebaceous tumors that are the hallmark of Muir-Torre Syndrome (MTS), a variant of hereditary nonpolyposis colorectal cancer (HNPCC) syndrome. A small sebaceous tumor was observed in three of four untreated Fhit +/+ mice, implying that very small sebaceous tumors occur spontaneously at a frequency similar to that of sebaceous tumors in the NMBA treated mice. Other tissues of the untreated mice were normal, including the esophagus, forestomach and squamocolumnar junction with the glandular stomach.

Sections from the fixed tissues were analysed by immunohistochemical detection of Fhit protein expression, to determine if the remaining Fhit allele had been inactivated in tumors. Epithelial cells lining the esophagus, forestomach and junction with the glandular stomach were positive for Fhit expression. In the esophagus, the basal epithelial cells stain less strongly than the overlying squamous cells (see FIG. 3A). All of the squamous papillomas and other tumors were Fhit negative, as illustrated in the examples shown in FIG. 3, B–F. Note especially the lack of Fhit expression in the sebaceous tumors shown in FIG. 3, E and F.

To compare the mouse sebaceous tumors to sebaceous tumors from Muir-Torre Syndrome cases, sebaceous tumor sections from two Muir-Torre Syndrome cases were analysed for expression of human Fhit. Fhit protein was detected in normal human hair follicle and sebaceous gland (FIGS. 4A and B) from the Muir-Torre Syndrome tumor sections. Fhit protein was not expressed in two human sebaceous tumors from case 1 (see FIG. 4D for example) but was expressed in the sebaceous tumor from case 2.

6.3 Genotypic Analysis

Murine Tissues

DNA was prepared from tail biopsies, as well as portions of the larger tumors of Fhit +/+ and +/− mice, in order to examine the integrity of the Fhit loci in tumors. To determine if the wild-type Fhit allele was deleted or rearranged in tumors, the DNA was typed for the presence of wild-type or targeted Fhit alleles by PCR amplification and both exon 5 alleles were detected. Tail and tumor DNAs were also digested with restriction enzymes and typed for presence of wild-type or altered Fhit alleles by Southern blot. The results shown in FIG. 5 reveal the presence of both wild-type and targeted Fhit exons 5 in tumors 21, 27 and 31 (FIG. 5, lanes 1, 3, 4). At least one copy of all other Fhit exons is retained in the tumors (compare lanes 1 and 2). Additional analyses of BamHI or XbaI digested tumor DNAs hybridized to probes for mouse exons 1–4, 7–9, and 4–10 did not reveal rearrangements or homozygous deletions of Fhit loci, although hemizygous deletions could not be ruled out. For example, densitometry analysis to compare intensity of bands for specific Fhit exons in lanes 1, 2 and 3 of FIG. 5 showed that the signal for exon 1 in lane 1 (tumor from mouse 21) was half as strong as the signal for exon 1 in lanes 2 and 3 relative to other exons. The signal for exon 5 in lanes 1 and 3 (tumor from mouse 21 and 27) is split into two bands, one near the top and one at the bottom of the lanes, representing the wild-type and mutant exons 5, respectively.

The Fhit protein is inactivated in all the NMBA-induced tumors through alteration of wild-type Fhit alleles within the mouse fragile site. To determine if NMBA had induced mutations in the wild-type Fhit allele, DNA from sebaceous tumors from mice 21, 27 and 31 and from squamous papillomas in mice 25 and 27 were also examined for mutations within Fhit exons 4 through 9. Primers flanking exons were used to amplify and sequence exons 4 through 9 in these tumors. No mutations were detected.

Human MTS syndrome is usually, if not always, caused by inactivation of mismatch repair genes and Muir-Torre syndrome tumors usually exhibit microsatellite instability (MSI). Tail and tumor DNAs were used as templates in PCR amplifications of ten microsatellite loci in a search for microsatellite instability. Results for three of these loci are shown in FIG. 6. Microsatellite instability was not observed at any of the mouse loci tested, demonstrating that the mouse MTS-like disease does not have an underlying mismatch repair defect.

Human Tissues

Not all Muir-Torre Syndrome cases have been shown to exhibit germline mutations of MSH2 or MLH1, nor do all Muir-Torre Syndrome tumors exhibit microsatellite instability, the hallmark of mismatch repair deficiency. It is possible that some Muir-Torre Syndrome cases with Fhit negative tumors are caused by germline mutation in the FHIT gene. The Muir-Torre Syndrome cases used in this study were analyzed for the presence of wild-type germline FHIT alleles. Restriction enzyme digestion of germline DNA from the two Muir-Torre Syndrome cases did not reveal alterations of the FHIT locus. Each FHIT exon was amplified from the two Muir-Torre Syndrome cases and the products sequenced. All germline FHIT exons from both cases showed wild-type sequences.

The majority of Muir-Torre Syndrome cases are due to germline mutations of the mismatch repair gene MSH2. Thus, Muir-Torre Syndrome tumors would be expected to show microsatellite instability. DNA from the two Fhit negative sebaceous tumors of Muir-Torre Syndrome case 1 and the Fhit positive tumor from case 2 did exhibit microsatellite instability with several of the five markers tested (for examples, see FIG. 6, lower panel).

TABLE 1

Tumor induction in Fhit +/+ and +/− mice at 10 weeks after NMBA treatment

| Mouse #, Genotype | Age (wks) | body wt. (g) | Phenotype | | | | Comments (by histology) |
|---|---|---|---|---|---|---|---|
| | | | Esoph. | Fore stomach | SCJ | Subcutis | |
| +/+ | | | | | | | |
| 40M | 46 | ↑3 | — | sm. T | — | — | adenoma |
| 37F | 39 | ↑2 | — | — | — | — | |
| 35F | 39 | ↑1 | — | — | — | — | |
| 29M | 39 | ↑4 | — | — | thick | — | |
| 25F | 39 | ↑4 | — | — | 7T$_+$3 mm | — | sq papillomas |
| 24F | 38 | ↑6 | thick | thick | — | — | papillary hyperplasia, esophagus |
| 22M | 34 | ↑3 | — | — | — | — | |
| 23M | 30 | ↑4 | — | — | — | — | |
| +/− | | | | | | | |
| 41M | 46 | ↑3 | — | 2T | few T | — | sq. carcinoma forestomach, sq. pap. SCJ |
| 39M | 46 | ↑2 | — | + | few T | — | sq. pap. forestomach, Barretts-like gastric mucosa SCJ |
| 38M | 46 | ↑4 | — | few sm. T | — | — | sq. pap. and adenoma forestomach |
| 31M | 39 | ↑4 | — | multiple T | — | T$_+$8 × 6 | sq. pap. and sq. carcinoma forestomach |
| 36F | 39 | ↑4 | + | multiple T | multiple T | T | sq. pap. esoph, forestomach, SCJ |
| 30M | 39 | ↑2 | — | + | — | — | sq. pap. forestomach |
| 34M | 38 | ↑8 | — | — | — | T$_+$9 × 5 | sebaceous adnexal tumor |
| 33M | 38 | ↑8 | + | multiple T | — | T$_+$7 × 6 | sq. pap. esoph and forestomach, seb. tumor |
| 32m | 38 | ↑6 | — | T | — | T$_+$5 × 6 | sq. pap. forestomach, sebaccous tumor |
| 28M | 38 | ↑3 | — | — | few T | — | sq. pap. |
| 27M | 38 | ↑4 | — | T.4 × 4 | few T | 2T$_+$7 × 5,2 × 3 | hyperplastic gastric mucosa, SCJ sq. pap. seb. tumor |
| 21M | 34 | ↑2 | — | T.2–3 mm | — | T$_+$7 × 4 | forestomach sq. papillomas; sebaceous tumor |

T. tumors. Some tumors were photographed, measured or samples taken for DNA for LOH analysis. 92% of +/− animals and 25% of +/+ animals showed evidence of tumorigenesis by visual inspection. Average age of +/+ group 38 weeks, average age of +/− group 39.9 weeks; body wt. column shows amount of wt. change during the experiment. sq. squamous; pap, papilloma; seb, sebaceous; SCJ, squamocolumar junction; esoph, esophagus. Untreated mice were examined for comparison. One untreated Fhit +/+ mouse showed no age matched abnormalities. three of four untreated fhit +/− mice showed an abdominal skin tumor and a second Fhit +/− mouse had an enlarged spleen.

TABLE 2

Incidence of tumors induced by multiple low NMBA doses in Fhit +/+ and +/− mice
Fraction of tumor bearing animals

| Week post-treatment | Fhit | Esoph[a] | Fore stomach[a] | SCJ[a] | Sebaceous[a] | Tumor Bearing Mice[a] |
|---|---|---|---|---|---|---|
| 6 wk | ++ | 1/10 | 1/10 | 0/10 | ND | 2/10 |
| 6 wk | +/− | 0/10[b] | 5/10 | 4/10 | ND | 7/10 |
| Fisher's exact test, 2-tailed | | P = 1.0 | P = 0.14 | P = 0.09 | | P = 0.07 |
| 10 wk | +/+ | 0/8 | 1/8 | 1/8 | 0/8 | 2/8 |
| 10 wk | +/− | 2/12 | 10/12 | 5/12 | 7/12 | 12/12 |

TABLE 2-continued

Incidence of tumors induced by multiple low NMBA doses in Fhit +/+ and +/− mice
Fraction of tumor bearing animals

| Week post-treatment | Fhit Esoph[a] | Fore stomach[a] | SCJ[a] | Sebaceous[a] | Tumor Bearing Mice[a] |
|---|---|---|---|---|---|
| Fisher's exact test, 2-tailed | P = 0.49 | P = .005 | P = 0.32 | P = 0.015 | P = 0.0007 |

[a] number of mice with tumors/respective number of mice.
[b] 1 esophagus showed dysplasia. The tumors of six weeks were mainly squamous papillomas. The tumors at ten weeks in the +/− mice were mostly squamous papillomas but two Fhit +/− mice had squamous carcinomas of the forestomach or junction; one Fhit +/+ and one +/− mouse at ten weeks showed a small adenoma of the forestomach. ND, non detected.

6.4 Discussion

The Fhit +/− Phenotype

The present invention relates to the inactivation of one Fhit allele in mice. Inactivation of one Fhit allele causes a tumor phenotype; this tumor phenotype is further influenced by carcinogen treatment. Observation of sebaceous tumors in 3 of 4 untreated Fhit +/− mice by one year of age revealed that inactivation of one Fhit allele in mice results in a tumor phenotype, although the full spectrum of tumors that will develop spontaneously in Fhit +/− and Fhit −/− mice is not yet known. 100% of NMBA treated Fhit +/− mice exhibited tumors compared to 25% of the treated Fhit +/+ mice, a highly significant difference, and none of the +/+ mice developed sebaceous tumors. Thus, absence of one Fhit allele caused susceptibility to sebaceous tumors and carcinogen induction of gastric tumors. As shown in Table 1, 5 of 12 Fhit +/− mice (under 1 yr. of age) showed large (>5×5 mm) sebaceous tumors, 3 of which were noted before autopsy. Sebaceous tumors have not been observed in untreated mice except by autopsy, which revealed small subcutaneous tumors (<2×2 mm) in 3 of 4 mice over 1 yr. old.

The tumors in both mouse strains do not express Fhit protein. NMBA treatment resulted in inactivation of both fragile Fhit alleles in the Fhit +/+ mice. It was necessary to inactivate only one Fhit allele in the +/− mice, thereby enhancing the frequency of tumor development, analogous to the 2-hits vs 1-hit required in human sporadic versus familial cancers. Because the only genetic difference between the Fhit +/+ and +/− mice is the targeted Fhit allele in the +/− mice, the second Fhit allele acts as the gatekeeper in tumor development, although the carcinogen has undoubtedly caused mutations of other suppressor genes in tumors of both mouse strains. Because Fhit +/− and −/− mice are fertile, long-lived and sensitive to carcinogen they will serve as useful models for carcinogen-induction of tumors of various organs.

The Role of NMBA

Although carcinogen treatment increases the frequency of occurrence of tumors in Fhit +/− mice, spontaneous tumors do occur. The carcinogen NMBA produces a disease in Fhit haploinsufficient mice that is similar to the Muir-Torre syndrome in humans. The carcinogen fulfills a role similar to the role of mismatch repair deficiency in human Muir-Torre Syndrome cases—both carcinogen and mismatch repair deficiency increase the frequency of alteration of the fragile Fhit locus, allowing selective growth of Fhit negative tumors. In the presence of the O6-meG mispairs, the Msh2-Msh6 complexes delay the already late replicating Fhit locus, so that replication is still incomplete in G2/M, leading to deletions in the fragile Fhit locus.

The organ specificity of NMBA is due to the presence of esophageal cytochrome P450 enzymes which bioactivate the carcinogen (Labuc and Archer, 1982, Cancer Res. 42:3181–3186). Although the N-7 position of guanine in DNA is the major site of alkylation, methylation at the O-6 position is more relevant for the biological activity (Fong et al., 1979, Int. J. Cancer 23:679–682), because the O-6-methylguanine adduct is associated with base mispairing and mutagenesis. As discussed above, Fhit +/− mice develop sebaceous tumors spontaneously, although the sebaceous tumors in the NMBA treated Fhit +/− mice were larger and more numerous. The affect of NMBA treatment on the development or progression of the sebaceous tumors will require further study.

Muir-Torre Syndrome

Muir described the coexistence of one or more sebaceous tumors with one or more visceral carcinomas; since then more than 150 cases have been reported (Kruse et al., 1998, Am. J. Hum. Genet. 63:63–70). Muir-Torre Syndrome is familial (Lynch et al., 1981, Arch. Intern. Med. 141:607–611) and has been found in families with hereditary nonpolyposis colorectal carcinoma (HNPCC) (Lynch et al., 1993, Gastroenterology 104:1535–1549). The most frequently observed internal neoplasm is colorectal carcinoma; thus, the syndrome shares clinical and pathological characteristics with hereditary nonpolyposis colorectal carcinoma. A large subgroup of Muir-Torre Syndrome cases exhibit microsatellite instability and germline mutations in MSH2 or MLH1 genes (Kruse et al., 1998, Am. J. Hum. Genet. 63:63–70). The Fhit deficient mouse tumors do not show microsatellite instability and loss of Fhit expression plays a role in their MTS-like disease; thus it is unlikely that the mouse syndrome involves mismatch repair deficiency.

In the mouse tumors the second Fhit allele was inactivated through deletion of one or more exons. This loss of Fhit protein resulted in a loss of a gatekeeper role, thereby resulting in tumor formation. It is known from studies of the human FHIT locus that biallelic deletions are observed and characterized by scanning the ~1.5 Mb locus by PCR-amplification using primer pairs spaced at 10–50 kb pair intervals. In the case of the mouse tumors, partial deletion of only the wild-type allele is necessary because the mutant allele is inactive. This type of deletion is difficult to observe in DNA from small tumors with noncancerous cells intermixed.

For a sebaceous tumor from Fhit +/− mouse 21, the exon 1 signal was diminished by half on Southern blot, implying the absence of one Fhit exon 1 from the wild-type allele. This is consistent with a shift in the epicenter of mouse Fhit fragility toward the 5' end of the gene (Glover et al., 1998, Cancer Res. 58:3409–3414) rather than being centered between exons 3 and 6 as in the human FRA3B (Huebner et al., 1998, Ann. Rev. Genet. 32:7–31).

If human and mouse Muir-Torre Syndrome cases arise through similar mechanisms, then the FHIT gene may be a target of damage in a fraction of mismatch repair deficient tumors, especially those with MSH2 deficiency, leading to Fhit protein loss and clonal expansion of Fhit negative cells. If Fhit inactivation is a frequent result of mismatch repair deficiency, and a frequent pathway to Muir-Torre Syndrome, then Fhit +/− mice will be predisposed to Muir-Torre Syndrome. The frequency of inactivation of the FHIT gene in human mismatch repair deficiency syndromes would be determined by examination of colon and other tumors with microsatellite instability for Fhit protein expression. Interestingly, Msh2 (Reitmair et al., 1996, Cancer Res. 56:3842–3849) and Msh6 (Edelmann et al., 1997, Cell 91:467–477) null mice exhibit sebaceous tumors at a low frequency, implying that crossing Fhit deficient mice with Msh2 deficient mice would lead to increased frequency of sebaceous and other tumors, compared to the spontaneous tumor frequency of either parental mouse strain.

Msh2 has been shown to form a complex with Msh3 or Msh6, these complexes have different mispair recognition specificities. The Msh2-Msh6 complex functions in repair of single base mispairs and small insertion/deletion mispairs. De Wind, et al. (1995) has reported that Msh2 mediates the toxicity of methylating agents, such as NMBA, and is required to suppress homologous recombination between slightly diverged DNA sequences. The types of chromosomal rearrangements observed in the human FHIT locus in cancer cells most often involves homologous recombination between slightly diverged sequences (Inoue, et al., 1997; Mimori, et al., 1999). Therefore, the absence of Msh2 in tumors will lead to increased chromosomal rearrangement at the FRA3B/FHIT fragile locus and result in loss of Fhit protein. In fact, it was previously observed that two of three human pancreatic cancer cell lines with high microsatellite instability had homozygous deletions within FHIT (Hilgers and Kern, 1999, Genes Chrom. Cancer 26:1–12).

Transgenic Mice as a Model for Muir-Torre Syndrome

The development of transgenic animals has provided biological and medical scientists with models that are useful in the study of disease. These animals are useful in testing pharmaceutical agents for utility in treating the disease, as well as in testing compounds that might cause or promote the development of the disease. In addition, transgenic animals are sources of cells, either tumor cells or non-tumor cells, for tissue culture that are useful in studying causes of a particular disease.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications, including patents and scientific literature, are cited herein, the disclosures of which are incorporated by reference in their entireties for all purposes.

What is claimed is:

1. A transgenic mouse the genome of which contains a disruption in the mouse FHIT gene, wherein said disruption comprises a termination codon in exon 5 of the FHIT gene, and wherein said mouse (a) has increased susceptibility to visceral and sebaceous tumors relative to FHIT +/+ mice, or (b) displays increased tumor formation upon being exposed to N-nitrosomethylbenzlamine relative to FHIT +/+ mice that have been exposed to N-nitrosomethylbenzlamine.

2. The transgenic mouse of claim 1, wherein said disruption of the FHIT gene is homozygous.

3. The transgenic mouse of claim 1, wherein said disruption of the PHIT gene is heterozygous.

4. The transgenic mouse of claim 2 or 3, said mouse having increased susceptibility to visceral and sebaceous tumors relative to FHIT +/+ mice.

5. The transgenic mouse of claim 2 or 3, wherein said mouse displays increased tumor formation upon being exposed to N-nitrosomethylbenzlamine relative to FHIT +/+ mice.

6. A transgenic mouse, wherein said mouse is chimeric for a disruption in the mouse FHIT gene, wherein said disruption comprises a termination codon in exon 5 of the FHIT gene, and wherein FHIT +/− progeny of said mouse (a) have increased susceptibility to visceral and sebaceous tumors relative to FHIT +/+ mice, or (b) display increased tumor formation upon being exposed to N-nitrosomethylbenzlamine relative to FHIT +/+ mice that have been exposed to N-nitrosomethylbenzlamine.

7. The transgenic mouse of claim 6, wherein said disruption of the FHIT gene is in both germline and somatic cells.

8. A method of testing carcinogenicity of a molecule, comprising:

(a) administering said molecule to the transgenic mouse of claim 1, 7, 2 or 3; and (b) comparing the rate of tumor formation in said transgenic mouse with a control mouse of the same genotype to which the molecule is not administered;

wherein an increased rate of tumor formation in the transgenic mouse following administration of the test molecule, as compared to the rate of tumor formation in the control mouse, is indicative that the molecule is carcinogen.

9. A method of testing the therapeutic efficacy of a molecule in treating or preventing cancer comprising:

(a) administering said molecule to the transgenic mouse of claim 1, 7, 2 or 3; and (b) comparing the rate of tumor formation in said transgenic mouse with a control mouse of the same genotype to which the molecule is not administered;

wherein a reduced rate of tumor formation in the transgenic mouse following administration of the test molecule, as compared to ihe rate of tumor formation in the control mouse, is indicative that the molecule has therapeutic or prophylactic value for cancer.

10. The method of claim 9, wherein the cancer is a gastrointestinal cancer.

11. The method of claim 9, where in the cancer is Muir-Torre Syndrome-related cancer.

12. The method of claim 9, wherein the cancer is hereditary non-polyposis colorectal cancer.

* * * * *

UNITED STATES PATENT AND TRADEMARK OFFICE
CERTIFICATE OF CORRECTION

PATENT NO. : 6,924,414 B2
DATED : August 2, 2005
INVENTOR(S) : Carlo M. Croce and Frances K. Huebner It is certified that error appears in the above-identified patent and that said Letters Patent is hereby corrected as shown below:

Column 45,
Line 27, delete "PHIT" and insert -- FHIT --.

Column 46,
Line 26, amend to recite -- a -- carcinogen.
Line 43, delete "where in" and insert -- wherein --.

Signed and Sealed this

First Day of November, 2005

JON W. DUDAS
*Director of the United States Patent and Trademark Office*